United States Patent
Persson et al.

(10) Patent No.: US 10,603,403 B2
(45) Date of Patent: Mar. 31, 2020

(54) ACRYLIC CEMENTS FOR BONE AUGMENTATION

(71) Applicant: INOSSIA AB, Stockholm (SE)

(72) Inventors: Cecilia Persson, Uppsala (SE); Alejandro Lopez, Stockholm (SE)

(73) Assignee: INOSSIA AB, Stockholm (SE)

( * ) Notice: Subject to any disclaimer, the term of this patent is extended or adjusted under 35 U.S.C. 154(b) by 0 days.

(21) Appl. No.: 14/783,019

(22) PCT Filed: Apr. 7, 2014

(86) PCT No.: PCT/SE2014/050429
§ 371 (c)(1),
(2) Date: Oct. 7, 2015

(87) PCT Pub. No.: WO2014/168565
PCT Pub. Date: Oct. 16, 2014

(65) Prior Publication Data
US 2016/0038631 A1    Feb. 11, 2016

(30) Foreign Application Priority Data
Apr. 8, 2013   (SE) ...................................... 1350437

(51) Int. Cl.
*A61L 24/06* (2006.01)
*A61L 27/50* (2006.01)
*A61L 24/00* (2006.01)
*A61L 27/16* (2006.01)

(52) U.S. Cl.
CPC ............ *A61L 24/06* (2013.01); *A61L 24/001* (2013.01); *A61L 24/0015* (2013.01); *A61L 27/16* (2013.01); *A61L 27/50* (2013.01); *A61L 2300/25* (2013.01); *A61L 2300/406* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2,574,753 A | 11/1951 | Opp et al. | |
| 7,569,621 B2 | 8/2009 | Kuhn et al. | |
| 2002/0156483 A1* | 10/2002 | Voellmicke | A61B 17/8822 606/93 |
| 2006/0041033 A1 | 2/2006 | Bisig et al. | |
| 2006/0293407 A1 | 12/2006 | Kuhn et al. | |
| 2007/0031469 A1 | 2/2007 | Kuhn et al. | |
| 2012/0022542 A1* | 1/2012 | Boger | A61L 27/46 606/94 |

FOREIGN PATENT DOCUMENTS

WO   2010/112955 A1   10/2010

OTHER PUBLICATIONS

Ewis, G., J. Biomed. Mater. Res. (Appl. Biomater.) 38: 155-182 (1997).*
Lam et al., In Vitro characterization of low modulus linoleic acid coated strontium-substituted hydroxyapatite containing PMMA bone cement, Journal of biomedical Materials Research B: Applied Biomaterials, 96B:76-83 (online Nov. 4, 2010).
Lopez et al., Low-modulus PMMA bone cement modified with caster oil, Bio-Medical Materials and Engineering; 21;323-332. (2011).
Vieira Da Cunha et al., Study of Castor Oil Poly (Methyl Methacrylate) Semi-Interpenetrating Polymer Network (SIPN) Reaction Parameters Using a 2 3 Factorial Experimental Design, Materials Research, vol. 7, No. 4, p. 539-543 (2004).
Ying et al., Study on Castor Oil Polyurethane/Poly(methyl methacrylate) AB Crosslinked Polymers, Chinese Journal of Polymer Science, vol. 9, No. 1, p. 31-38 (1991).
Newitt et al., In Vivo Assessment of Architecture and Micro-Finite Element Analysis Derived Indices of Mechanical Properties of Trabecular Bone in the Radius, Osteoporosis International, 13:6-17 (2002).
Lopez et al., Compressive mechanical properties and cytocompatibility of bone-compliant, linoleic acid-modified bone cement in a bovine model, Journal of the Mechanical Behavior of Biomedical Materials, 32:245-256 (online Jan. 15, 2014).
Vazquez et al., Characterization of New Acrylic Bone Cements Prepared with Oleic Acid Derivatives, Journal of Biomedical Materials Research, 63(2):88-97 (2002).
Kong et al., Sequential Interpenetrating Polymer Networks Produced from Vegetable Oil Based Polyurethane and Poly(methylmethacrylate), Biomacromolecules, 9:2221-2229 (2008).
Persson et al, "The effect of unsaturated fatty acid and triglyceride oil addition on the mechanical and antibacterial properties of acrylic bone cements," Journal of Biomaterials Applications, pp. 1-11 (Apr. 21, 2015).

* cited by examiner

Primary Examiner — David J Blanchard
Assistant Examiner — Daniel F. Coughlin
(74) Attorney, Agent, or Firm — Porter Wright Morris & Arthur LLP

(57) ABSTRACT

The embodiments relate to an injectable composition for a bone cement material comprising a dry powder component, a liquid component and a modifier configured to modify a Young's modulus of the bone cement material. The modifier is linoleic acid or a derivative thereof and is present in a concentration of 0.1 to 12 v/v of the liquid component.

22 Claims, 24 Drawing Sheets

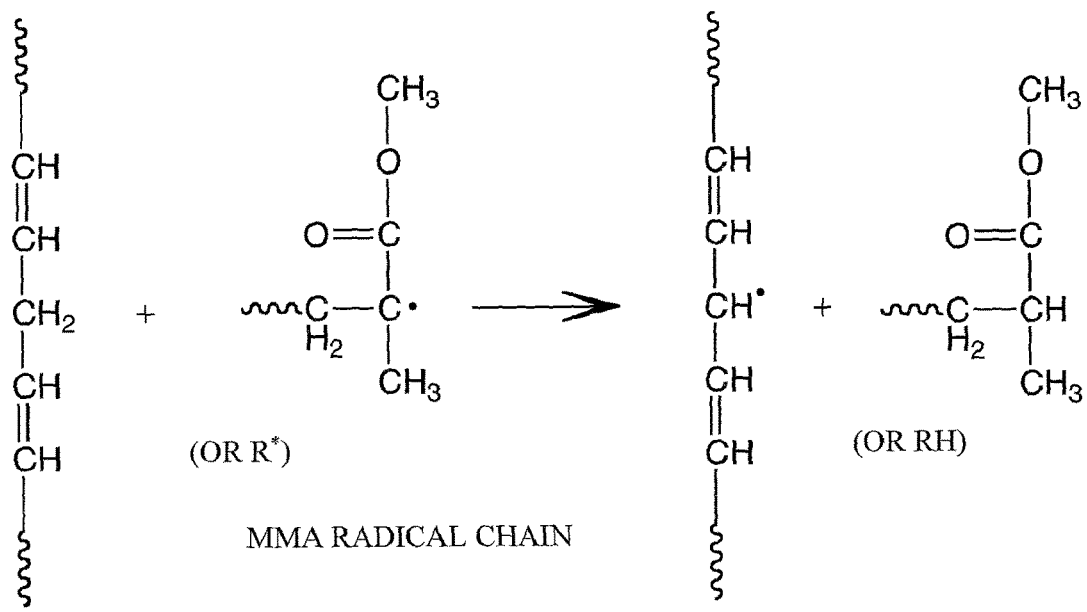
LINOLEIC ACID OR OTHER
UNSATURATED FATTY ACID
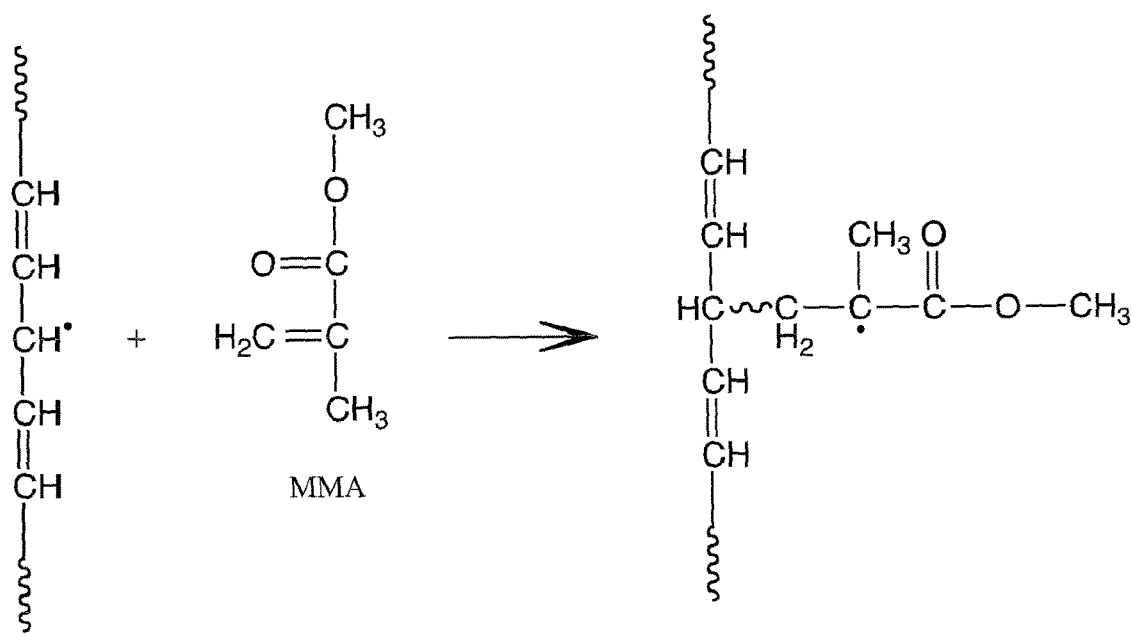
Fig. 1

| | |
|---|---|
| Calcium phosphate cement | 5 mm |
| Vertecem (incl. 30% BaSO$_4$) | 4 mm |
| | 3 mm |
| Vertecem (incl. 40% ZrO$_2$) | 2 mm |
| | 1 mm |
| Simplex P | Al |
| Simplex P (+20% BaSO$_4$) | |
| Osteopal V (incl. 45% ZrO$_2$) | |
| Osteopal V (+ 17.8% castor oil) | Trabecular bone |
| Osteopal V (+ 0.75% linoleic acid) | |
| Osteopal V (+ 17.5% oleic acid) | |

Fig. 11

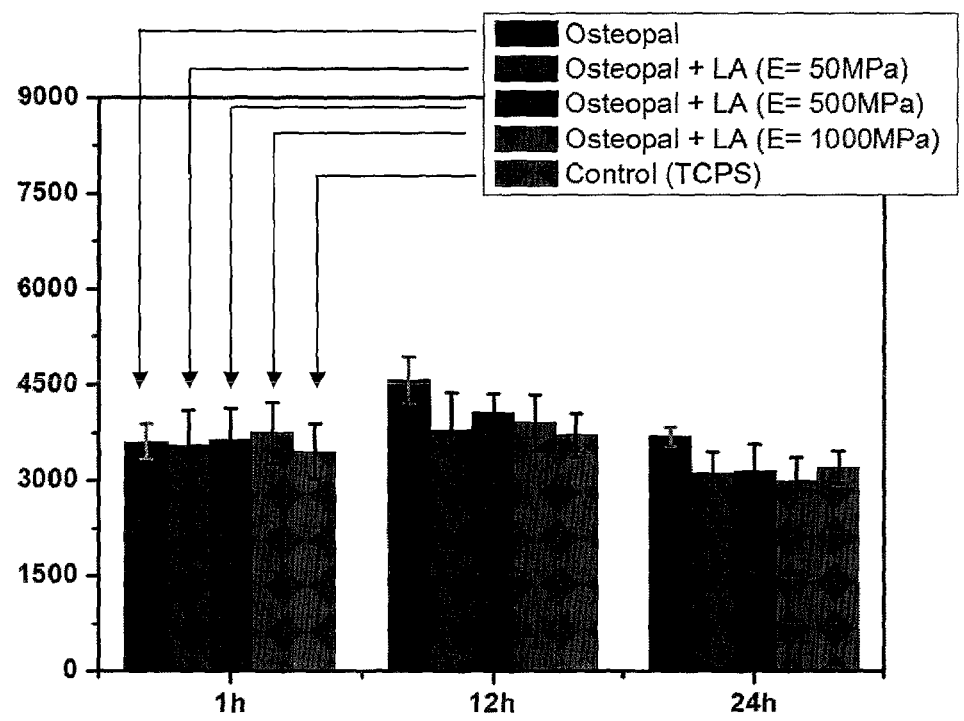
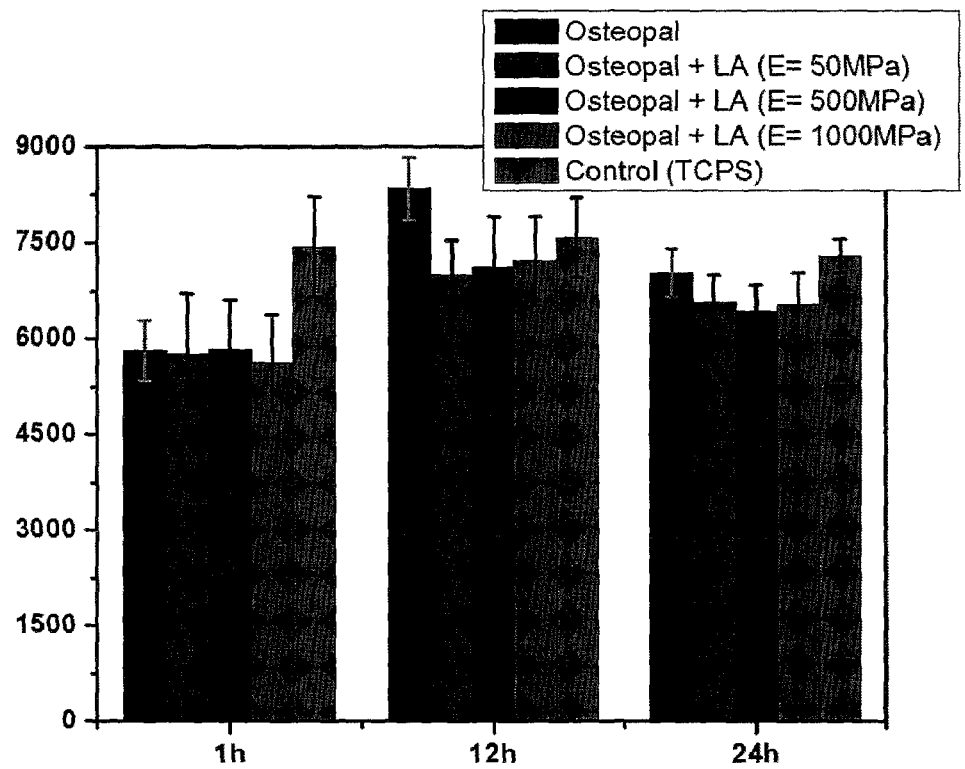
EXTRACTION TIME
Fig. 12

PFig. 16

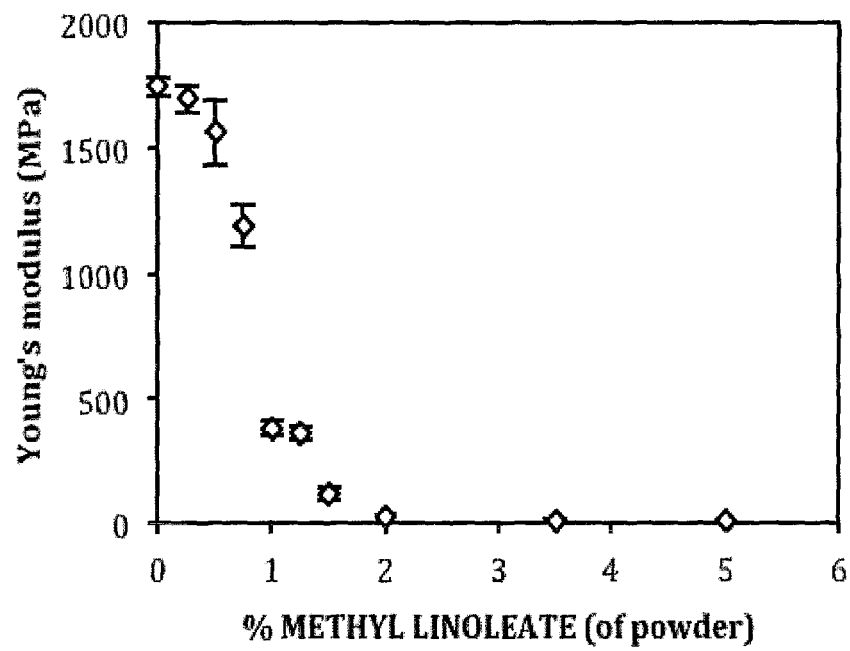
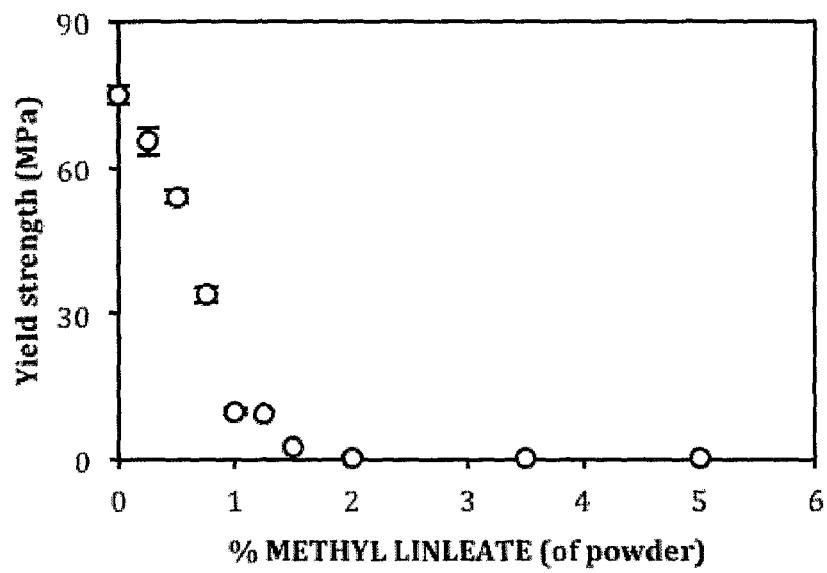
Fig. 17

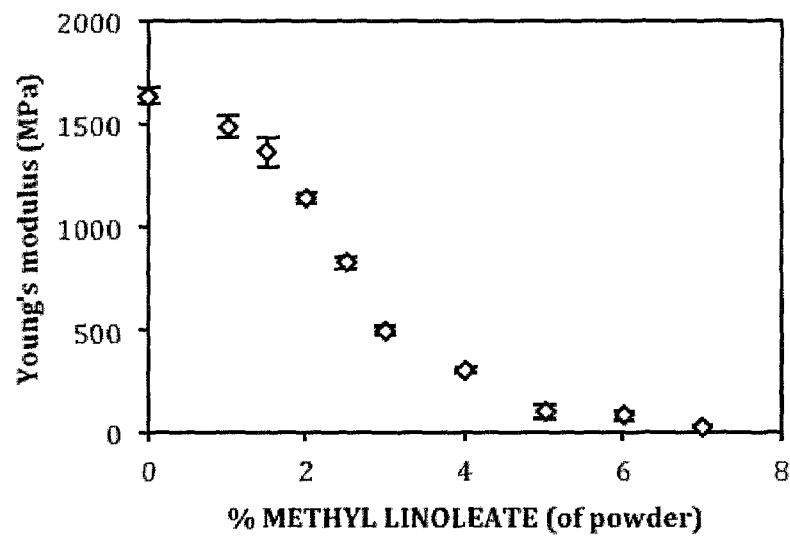
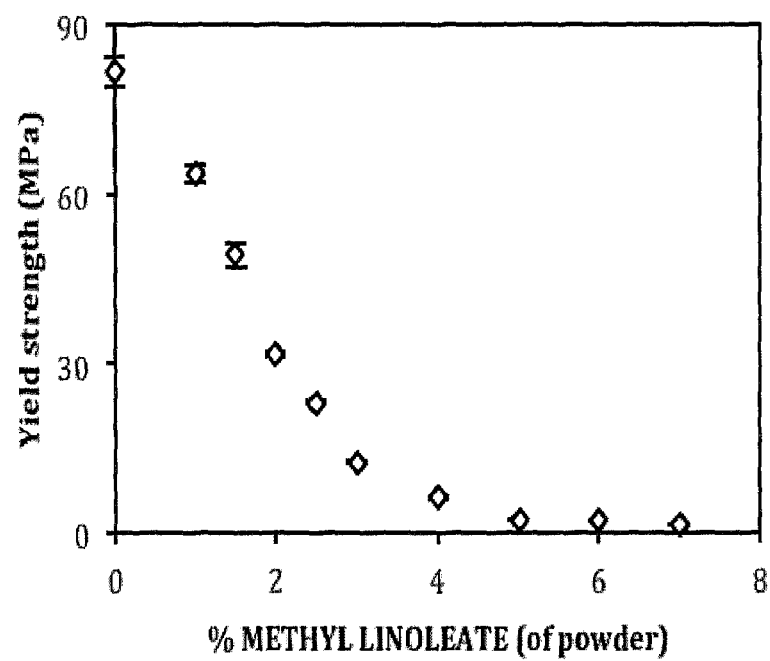
Fig. 18

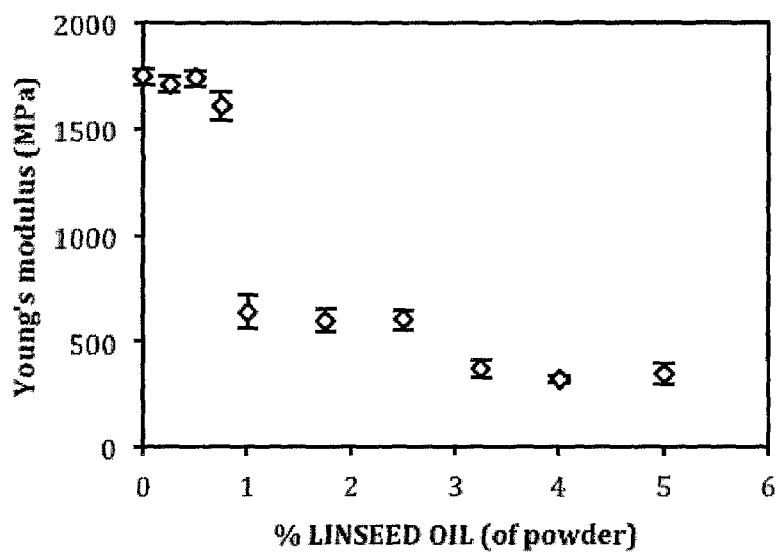
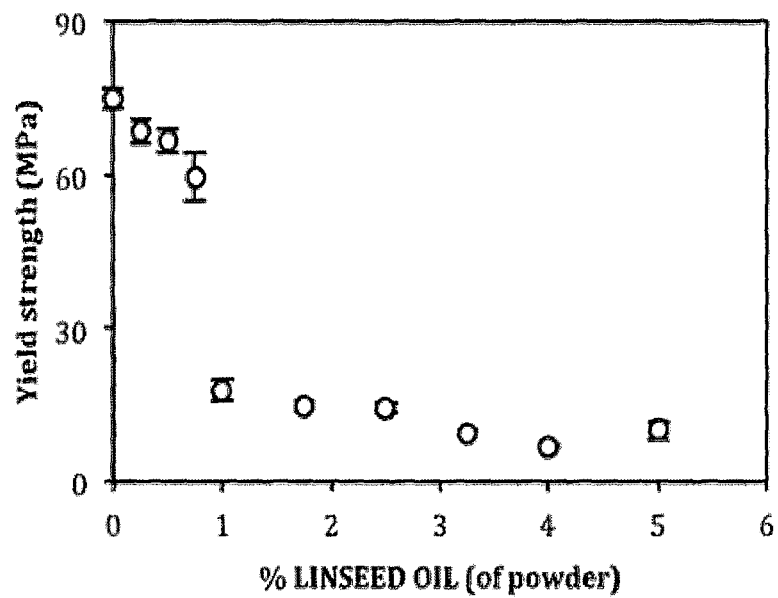
Fig. 19

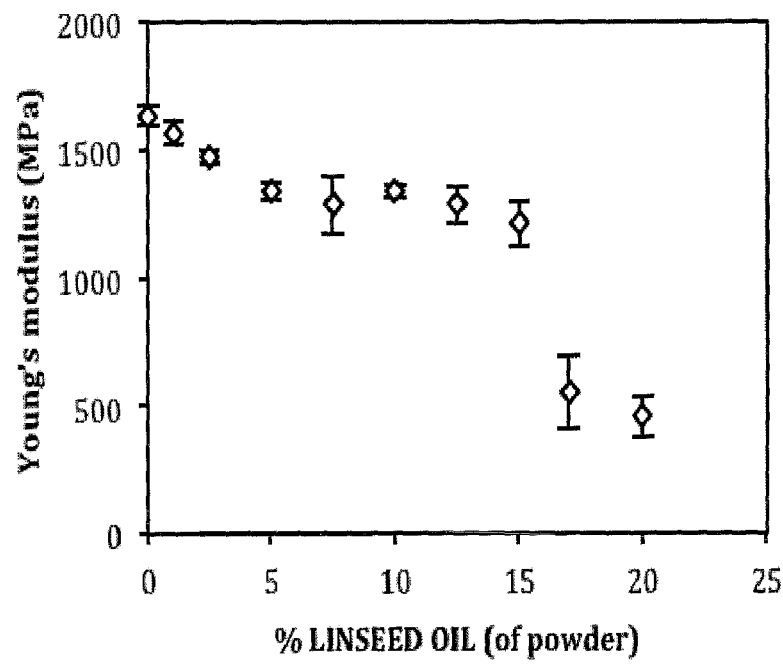
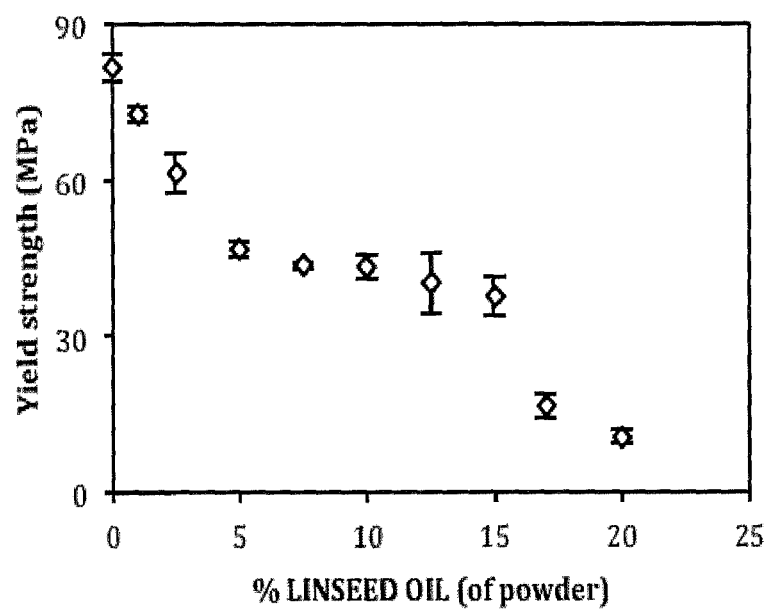
Fig. 20

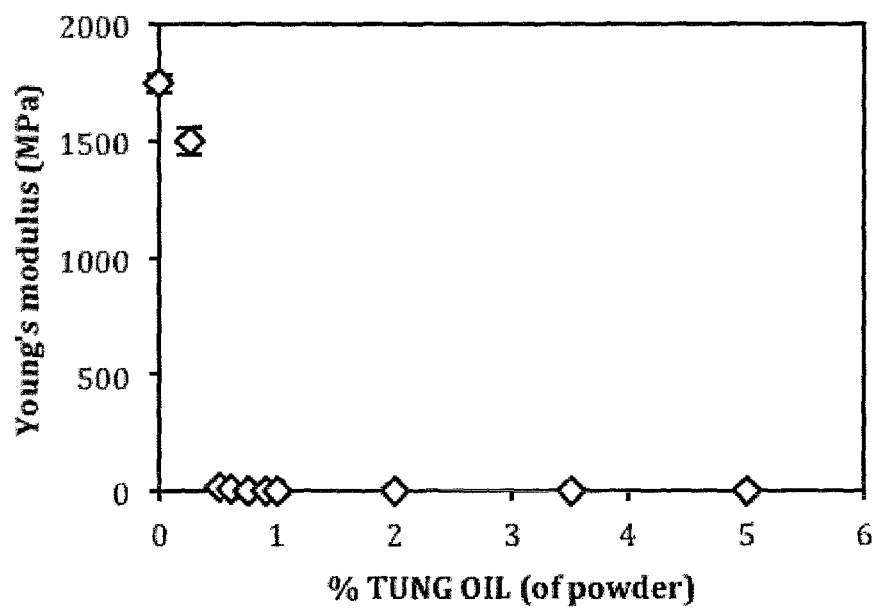
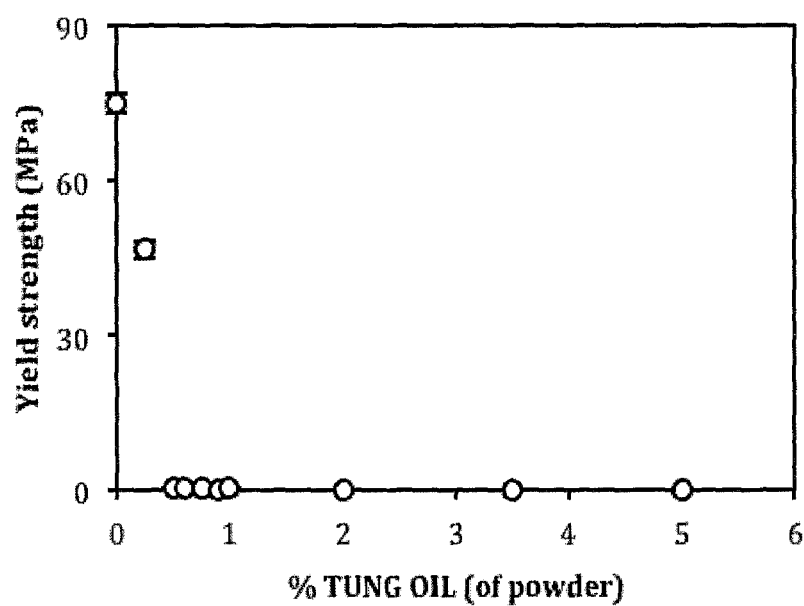
Fig. 21

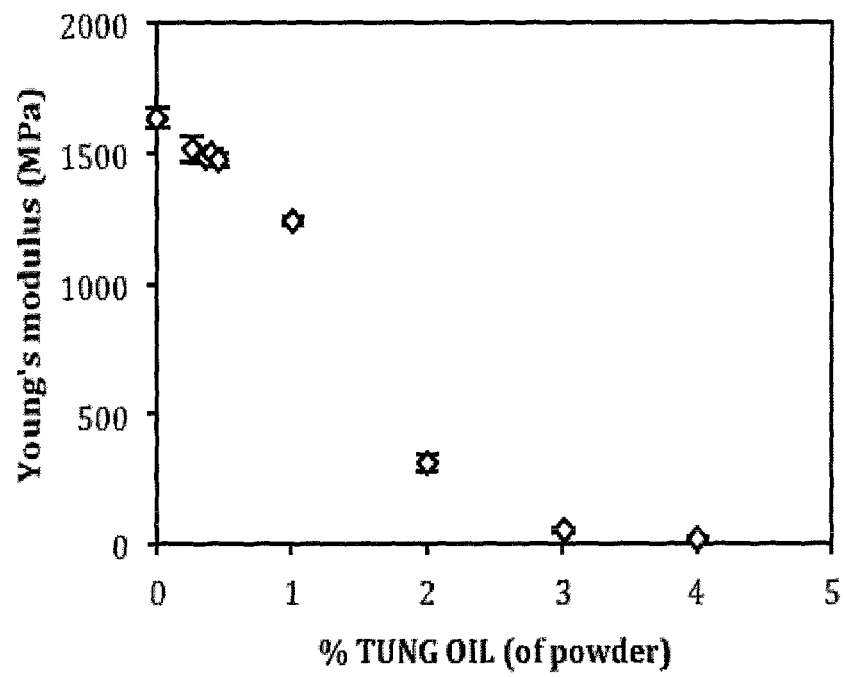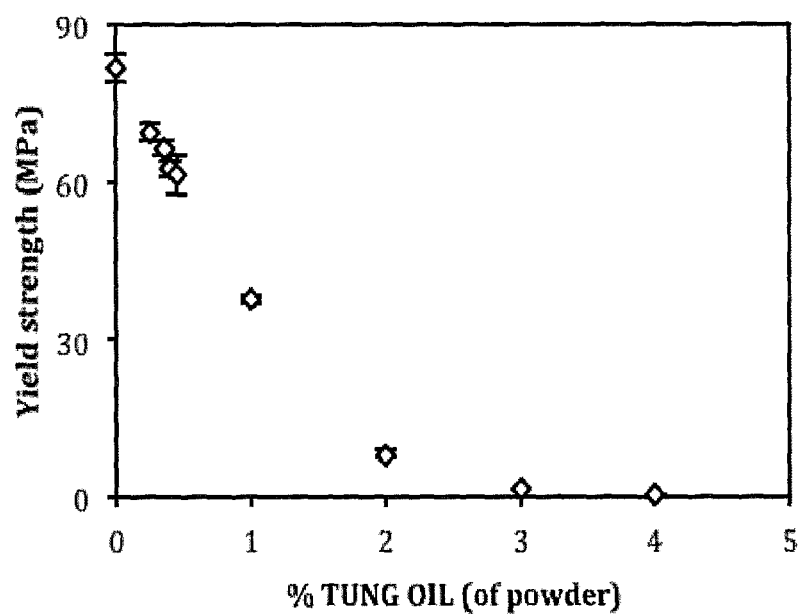
Fig. 22

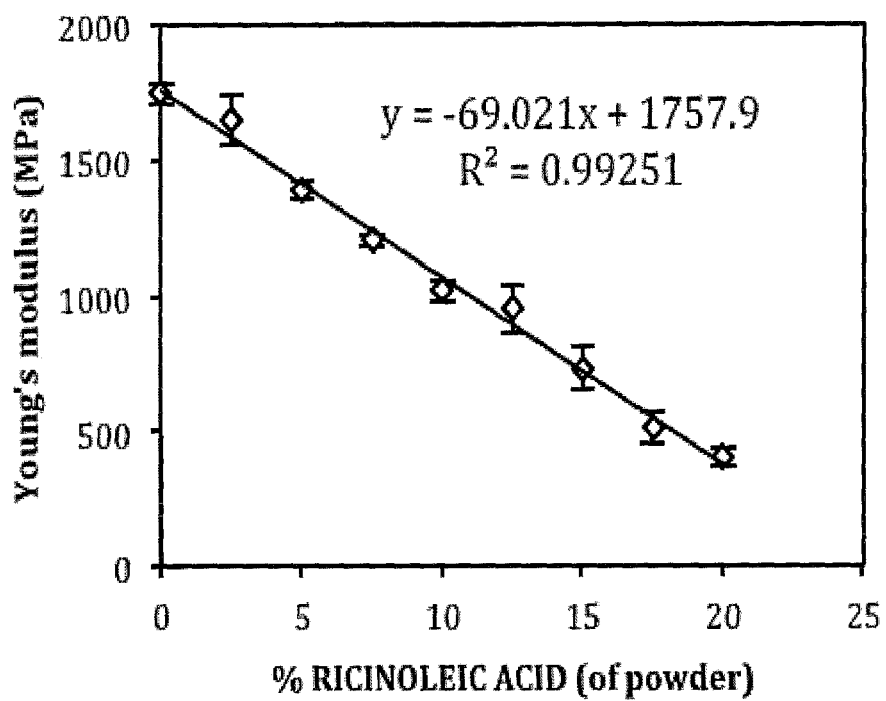
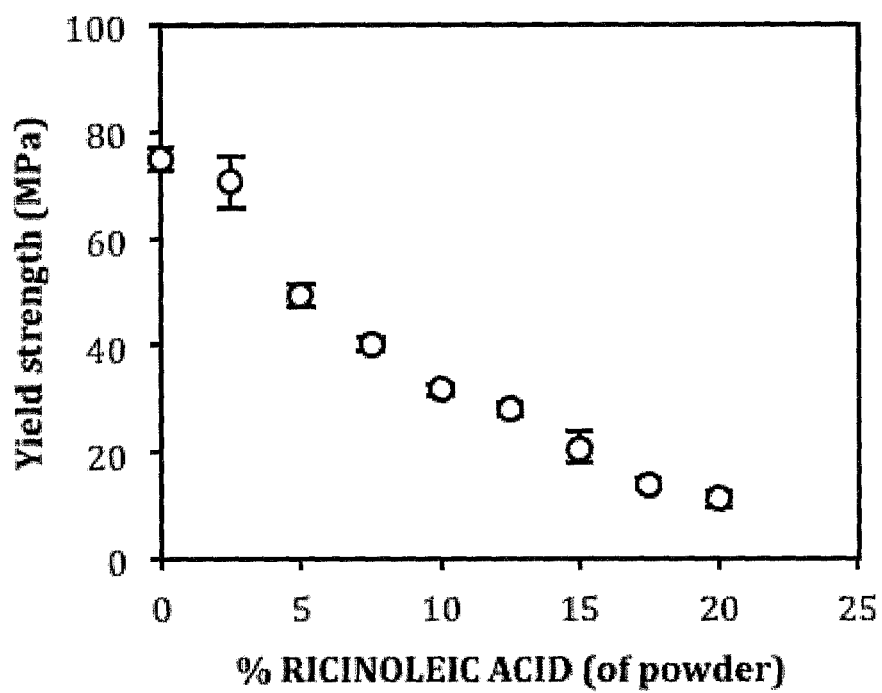
Fig. 23

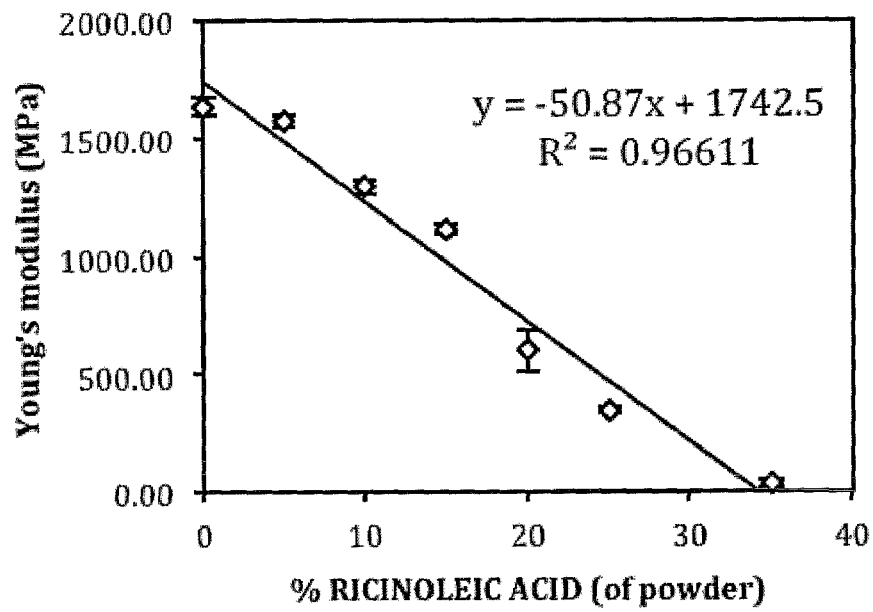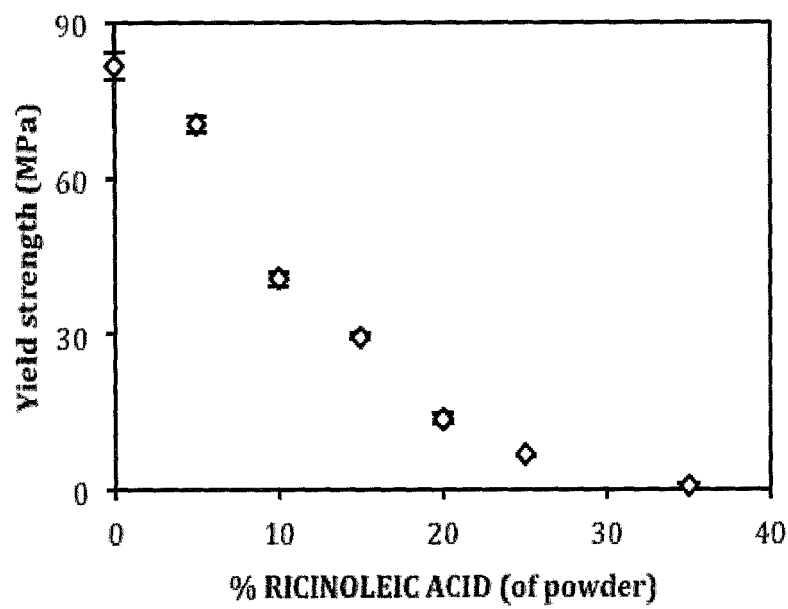
Fig. 24

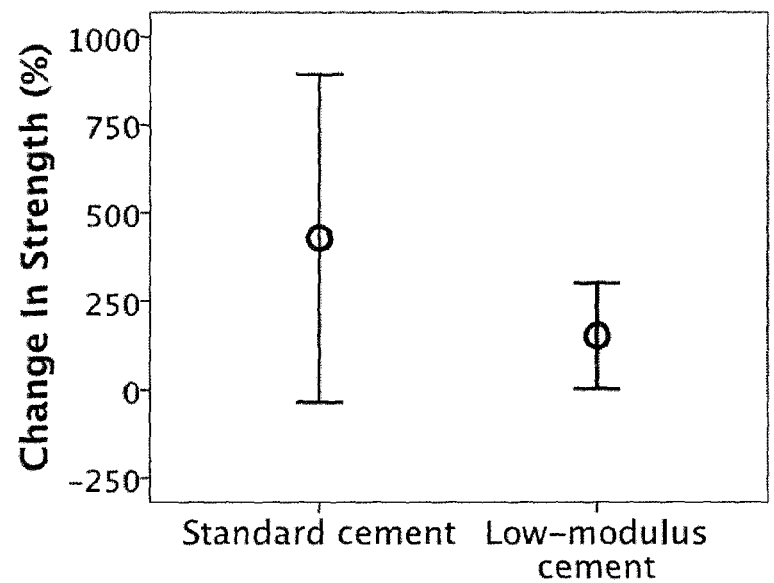
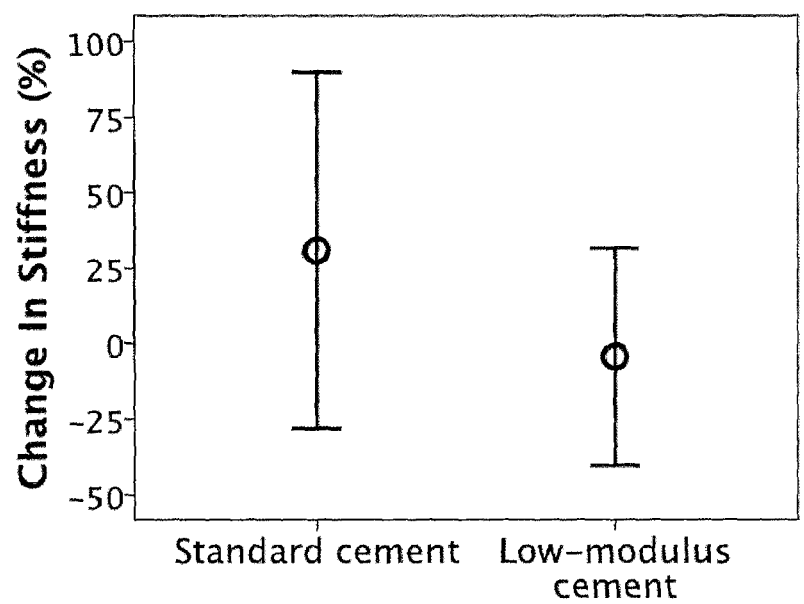
Fig. 27

ACRYLIC CEMENTS FOR BONE AUGMENTATION

TECHNICAL FIELD

The present embodiments relate to a medical composition of acrylic cement for augmenting bony tissue.

BACKGROUND

Acrylates, typically poly(methyl methacrylate) (PMMA), are bioinert materials commonly used to repair and augment spinal compression fractures and to fixate hip and knee implants. Since these materials have a Young's modulus that is much higher than that of human cancellous bone, they may affect the biomechanics negatively, which may promote fractures in the tissues adjacent to the augmented one. The development of PMMA cement with a lower modulus is highly desirable since it could reduce the incidence of subsequent complications, such as fractures. Further tailoring the Young's modulus by small changes in chemical composition, would give the possibility to adapt the cement to e.g. the degree of osteoporosis of a certain patient, which would make the cement patient-specific. Physical or chemical modification of the material would give the possibility to control its Young's modulus.

Various approaches to produce low-modulus PMMA bone cements have been documented.

One approach is to induce porosity in the material. A porous material could present a lower Young's modulus and also allow for a certain bone ingrowth. It has been shown that porous polymeric scaffolds may support osteoblast differentiation and subsequent bone formation (Shimko, White, et al. 2003).

Moreover, pores may act as drug reservoirs. The introduction of drugs into bone cements is of great importance in order to help the patients to recover upon surgery and to obtain the maximum benefit out of the cement. Drugs, such as bisphosphonates, may be beneficial to patients suffering from osteoporosis, due to the importance of these drugs in bone regeneration. Moreover, antibiotics, such as vancomycin, can help avoid possible infections at the site of injection. A porous structure may help to control the release of previously mentioned drugs or other types of growth factors from the material.

Currently, drugs can be directly mixed into the PMMA powder and thereby incorporated into the cement. This approach, however, limits the ability to control the release of drugs into the body, since it principally depends on the relative surface area of the total material injected. For instance, porous PMMA cement has been prepared by using water-soluble porogen salts, such as NaCl (Shimko and Nauman 2007). Porogen leaching is a common technique to create porous polymeric materials. In this example, the salt is added during the mixing step and it remains intact during the polymerization process. Upon setting, the salt is gradually dissolved out of the polymer, leaving pores behind. However, methods such as porogen leaching are not applicable to certain procedures, such as vertebroplasty.

Similarly, other studies (Shimko and Nauman 2007; van Mullem, de Wijn, et al. 1988) used an aqueous solution based on carboxymethyl cellulose to create a porous PMMA. This material has been successfully used in craniofacial surgery in its malleable form (Bruens, Pieterman, et al. 2003) but there are no reports on its usage while still being in the injectable stage.

The addition of a sodium hyaluronate solution has also been proposed to control the modulus and the porosity of PMMA bone cements (Boger, Bisig, et al. 2008; Boger, Bohner, et al. 2008). The sodium hyaluronate solution acts as a pore-forming phase due to its immiscibility. Unfortunately, it was later reported (Beck and Boger 2009) that this method gave rise to unacceptably high release of polymer powder particles. Some methods exist to induce porosity in PMMA using oils. Such procedures are described in detail in U.S. Pat. No. 4,594,207 and international application publication WO90/05007. However, these methods involve heating above the critical temperature of the mixture and these values are reported to be above 150° C. Such high temperatures are not applicable to injectable formulations and are intolerable for in vivo applications.

Another simple approach in order to decrease the modulus of PMMA bone cements may be their chemical modification, namely, copolymerization or grafting with somewhat more flexible species containing relatively long chains. These long chains could act as spacers between the polymer chains, somewhat lowering the glass transition temperature and facilitating the chain motion, which would result in a lower Young's modulus. Large molecules, may also act as physical spacers/plasticizers, if not grafted to the main polymer chain or network. The addition of plasticizers would also result in a lower Young's modulus. Chemical or physical modifiers can for instance be obtained from natural sources.

Polymers from renewable sources have quickly emerged due to their relatively low-cost and unique properties (Sehina Güner, Yağci, et al 2006). Natural oils, which consist mainly of triglycerides, can be obtained from a wide variety of renewable sources. Oil is thereby referred to as a triglyceride that is liquid at room temperature. Moreover, a triglyceride is obtained upon esterification of a glycerol molecule with three fatty acids. Most fatty acids are unsaturated, which means that they contain one to several double bonds in their chemical structure. These double bonds are susceptible to attack by free radicals, making these compounds able to be incorporated into the polymer during radical polymerization of PMMA.

Copolymerization of unsaturated fatty acids and their esters with unsaturated compounds is described in U.S. Pat. No. 2,574,753. However, their method is bulk polymerization and involves heating up the reactants to relatively high temperatures, which are not suitable for in vivo applications.

Natural oils have been used to fabricate interpenetrating polymer networks based on polyurethane and poly(methyl methacrylate). However, these synthesis methods also require relatively long polymerization times and high temperatures (Oliveira et al. 2004; Kong and Narine 2008), which are not suitable for in vivo applications.

Oleic acid derivatives such as 4-N,N-dimethylaminobenzyl oleate and oleyloxyethyl methacrylate have been used as total substitute for N,N-dimethyl-p-toluidine and partial substitute for methyl methacrylate, respectively. These formulations, although with improved handling properties, were not intended to lower the Young's moduli of the materials, whose values were between 1.20 and 3.58 GPa (Vázquez et al. 2001).

Another study (Lam et al. 2010) has shown that the incorporation of up to 20 wt % linoleic acid functionalized strontium-substituted hydroxyapatite particles, can lower the modulus down to 1800 MPa (12% respect to the control). Additionally, incorporation of up to 15 vol % linoleic acid substituting the monomer, can reduce the modulus down to 774 MPa (43% respect to the control). However, these particles are produced through a relatively complicated method and the researchers reported decreased cell viability due to unconverted monomer for this formulation.

WO 2004/071543 claims the use of a third hydrophobic component, such as fatty acids and other triglycerides, as possible solvents for organic radiopaque agents. However, the third component in this formulation is not intended to react with the PMMA or to be covalently incorporated into the cement but washed off from the cement instead. In fact, it is mixed in after the mixing of the powder and the liquid. US 2006/0293407 and US 2007/0031469 describe the use of esterified fatty acids as solvents for dyes.

SUMMARY

It is a general objective to provide an improved injectable composition for a bone cement material.

It is a particular objective to provide a modifier useful for modifying a Young's modulus of a bone cement material.

These and other objectives are met by embodiments described herein.

An aspect of the embodiments relates to an injectable composition for a bone cement material comprising a dry power component, a liquid component and a modifier configured to modify a Young's modulus of the bone cement material. In an embodiment, the modifier is linoleic acid or a derivative thereof and is present in a concentration of 0.1 to 12 v/v of the liquid component.

Another aspect of the embodiments relates to a bone cement obtainable by mixing a liquid component comprising i) methyl methacrylate (MMA) monomer and a chemical activator, preferably N,N-dimethyl-p-toluidine, with a modifier in terms of linoleic acid or a derivative thereof, present in a concentration of 0.1 to 12 v/v of the liquid component to form a homogenous solution. The homogenous solution is mixed with a dry powder component comprising i) prepolymerized poly(methyl methacrylate) (PMMA) or a copolymer of PMMA and a pharmaceutically acceptable polymer, preferably a copolymer of PMMA and polystyrene, ii) a radical initiator, preferably benzoyl peroxide, and iii) optionally a radiocontrast agent, preferably barium sulfate, strontium salt or zirconium dioxide.

A further aspect of the embodiments relates to a method of producing an injectable composition for a bone cement material. The method comprises mixing a dry powder component, a liquid component and a modifier to form said bone cement material. In an embodiment, the modifier is linoleic acid or a derivative thereof, and is present in a concentration of 0.1 to 12 v/v of the liquid component.

Yet another aspect of the embodiments relates to use of a modifier at a concentration of 0.1 to 12 v/v of a liquid component of a bone cement material to modify Young's modulus of the bone cement material formed by mixing the liquid component, the modifier and a dry powder component. In an embodiment, the modifier is linoleic acid or a derivative thereof.

An additional aspect of the embodiments relates to use of an injectable composition for a bone cement material according to above or a bone cement according to above in a medical application selected from a group consisting of hip arthroplasty, knee arthroplasty, small joint arthroplasty, dental implantology, percutaneous vertebral augmentation, such as kyphoplasty or vertebroplasty, femeroplasty, treatment of metastatic spinal disease, prosthetic fixation, screw augmentation, sacroplasty, bone substitution, cranioplasty, plastic surgery application, maxillofacial surgery, bone augmentation, fracture healing, disc replacement, cartilage repair, oncological treatment, and cemented surgeries.

A further aspect of the embodiments relates to a kit for producing an injectable composition for a bone cement material. The kit comprises a container comprising a liquid component and a container comprising a modifier in terms of linoleic acid or a derivative thereof at an amount corresponding to a concentration of 0.1 to 12 v/v of the liquid component when mixing the modifier and the liquid component. The kit also comprises a container comprising a dry powder component. The kit further comprises instructions for mixing the modifier and the liquid component to form a homogenous solution and instructions for mixing the dry powder component and the homogenous solution to form the injectable composition for the bone cement material.

Yet another aspect of the embodiments relates to a method of producing a subject-specific injectable composition for a bone cement material. The method comprises determining a target Young's modulus of the bone cement material based on a bone mineral density of a subject. The method also comprises determining a concentration of a modifier within a range of 0.1 to 12 v/v of a liquid component based on the target Young's modulus. The method further comprises mixing a dry powder component, the liquid component and the modifier to form the bone cement material. In an embodiment, the modifier is linoleic acid or a derivative thereof and is present in the determined concentration.

The embodiments enable control of the Young's modulus of a bone cement material without greatly affecting the cell viability.

Other objects, advantages and novel features of the present embodiments will become apparent from the following detailed description of embodiments when considered in conjunction with the appended examples.

BRIEF DESCRIPTION OF THE DRAWINGS

The embodiments, together with further objects and advantages thereof, may best be understood by making reference to the following description taken together with the accompanying drawings, in which:

FIG. 1 schematically illustrates methacrylation of linoleic acid.

FIG. 11 illustrates a radiography of specimens containing castor oil, linoleic acid, and oleic acid, according to examples 1-3 in comparison with other commonly used commercial bone cements.

FIG. 12 shows diagrams illustrating relative cell viability of Saos-2 cells (compared to a control culture in normal medium) maintained in extraction media from different linoleic acid containing bone cements for 1 and 3 days. The higher the RFU value, the higher is the cell viability.

FIG. 17 illustrates Young's modulus and yield strength of PMMA bone cement modified with methyl linoleate.

FIG. 18 illustrates Young's modulus and yield strength of PMMA bone cement Simplex P modified with methyl linoleate.

FIG. 19 illustrates Young's modulus and yield strength of PMMA bone cement modified with linseed oil.

FIG. 20 illustrates Young's modulus and yield strength of PMMA bone cement Simplex P modified with linseed oil.

FIG. 21 illustrates Young's modulus and yield strength of PMMA bone cement modified with tung oil.

FIG. 22 illustrates Young's modulus and yield strength of PMMA bone cement Simplex P modified with tung oil.

FIG. 23 illustrates Young's modulus and yield strength of PMMA bone cement Osteopal V modified with ricinoleic acid.

FIG. 24 illustrates Young's modulus and yield strength of PMMA bone cement Simplex P modified with ricinoleic acid.

FIG. 27 illustrates the percentage change in strength (left) and stiffness (right) of osteoporotic vertebral bodies after fracture and augmentation with standard and low-modulus cement.

DETAILED DESCRIPTION

Figure 2:
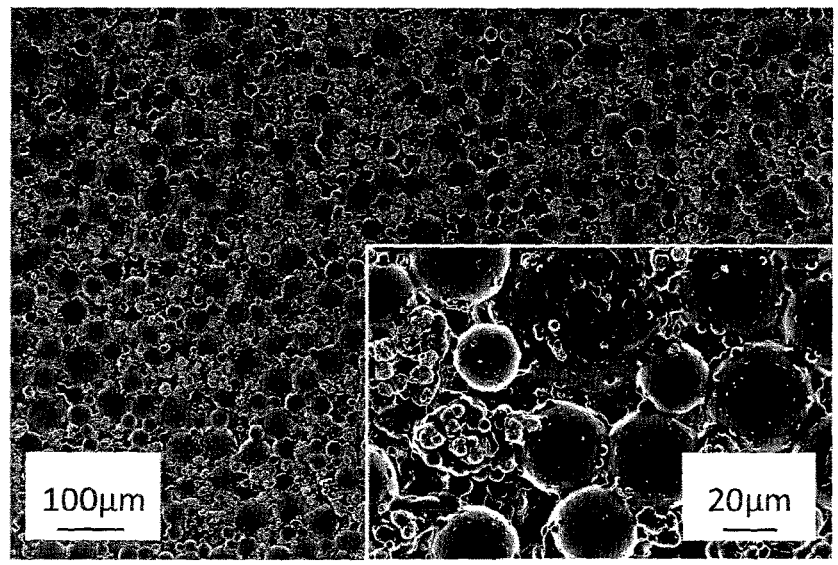
FIG. 2 illustrates a scanning electron micrograph of standard unmodified bone cement (300 and 2000×) showing low porosity. This figure is shown for comparison with examples 1 and 2.

Prior art has drawbacks with regard to being able to produce a bone tissue replacement with an adequate and adaptable Young's modulus and controlled drug release. The present embodiments provide a material and a simple manufacturing method that overcomes the above-mentioned hindrances, promotes osseointegration, and matches the mechanical properties to that of the surrounding bone tissue. This is achieved by modifying the bone cement using unsaturated fatty acids, triglyceride oils or their mixtures. The incorporation of unsaturated fatty acids or triglyceride oils into bone cements has multiple purposes:

a) To chemically modify the polymer architecture by acting as covalently attached spacers between the polymer chains.

b) To physically modify the polymer network by acting as plasticizers c) To modify the bone cement microstructure by inducing pore formation.

d) To enhance drug delivery from the cements

The first three modifications may, by different mechanisms, help reduce and control the Young's modulus, as well as the drug release from the bone cements. Chemical modification, by introduction of relatively long chains, such as fatty acids or triglyceride oils, can lower the Young's modulus by increasing the spacing and allowing the chains to better glide with respect to each other. On the other hand, unreacted fatty acids or triglyceride oils, can act as natural plasticizers by placing themselves in between the polymer chains, decreasing the glass transition temperature of the overall polymer and lowering the Young's modulus. Moreover, pores in the microstructure would reduce the density and result in a less compact more deformable material with a lower Young's modulus. Porosity may additionally promote osseointegration of PMMA and act as drug reservoirs in order to influence and ultimately control the drug release from the cements.

The present embodiments relate to an injectable formulation that sets upon mixing the liquid and the powder phase, the liquid phase containing unsaturated fatty acids or triglyceride oils. The reaction is initiated upon decomposing the peroxide in the powder phase by a chemical activator in the liquid phase rather than applying external heat, as is common in injectable bone cements. The free radicals can attack the double bonds in either the monomer or the unsaturated fatty acids forming an injectable acrylic cement that incorporates grafts or segments of fatty acids or triglyceride oils.

The formulations of the present embodiments give complete control of the Young's modulus, without greatly modifying the cell viability. For example, the use of up to only 6 v/v of liquid phase (1.5 w/w of total weight of cement) linoleic acid gives a Young's modulus of 250-900 MPa, depending on testing conditions, specimen size and quality of the additive.

The present embodiments are based on the fact that unsaturated fatty acids and/or triglyceride oils could be covalently incorporated into the polymer. Nevertheless, a plasticizing effect is still possible in case of existing unreacted fatty acid/oil so that tailoring the mechanical properties would, depending on the chemical nature of the modifier, be a contribution of both chemical and physical effects.

The present embodiments further describe the use of fatty acids and/or triglyceride oils as chemical bone cement modifiers to tailor the mechanical properties and/or the microstructure for tunable (lower) Young's modulus and/or improved drug release capabilities. Also, in the present embodiments, the esterified fatty acids are preferably mixed in the liquid monomer rather than in the powder. This will have little effect on the mechanistic behavior of the material, but improves the handling of the material and leads to a less complicated product.

An embodiment is directed towards an injectable bone cement comprising two parts:

(i) a solid phase based on pre-polymerized PMMA beads; and (ii) a liquid phase based on MMA monomer and a fatty acid or a triglyceride oil.

The solid phase typically comprises at least appropriate amounts of pre-polymerized PMMA, radical initiator (e.g. BPO), and a radiopaque agent (e.g. $ZrO_2$, $BaSO_4$). The liquid phase typically comprises at least appropriate amounts of MMA monomer, a fatty acid or a triglyceride oil, a chemical activator (e.g. DMPT), and a long-term storage stabilizer (e.g. hydroquinone). The fatty acid or triglyceride oil is preferably to be packed separately but may also be previously dissolved in the liquid component or added to it or the powder phase at various time points to control the microstructure.

Another embodiment is directed towards a method of producing an injectable PMMA-based product comprising the steps of:

a) providing a solid phase comprising at least PMMA beads, a radical initiator, a radiopacifier and optionally a drug, b) providing a liquid phase comprising at least MMA monomer, a fatty acid or a triglyceride oil, a chemical activator, and optionally a long term storage preservative, c) providing a modifier comprising at least a fatty acid or a triglyceride oil and optionally a drug and/or a long term storage preservative, and d) mixing the modifier and the liquid phase first followed by the solid phase, whereafter said injectable PMMA-based product is ready to be injected.

The product may be injected directly into the patient, or into a mold, e.g. when used as a spacer or in the form of beads for delivery of drugs, such as antibiotics.

Yet another embodiment relates to a kit for applications, such as vertebroplasty, kyphoplasty and general bone augmentation. The present embodiments utilize a mixing procedure similar to standard PMMA, allowing surgeons to work with confidence and familiarity. Such a kit comprises:

a) a solid phase, comprising at least PMMA beads, a radical initiator, a radiopacifier and optionally a drug, b) a liquid phase comprising at least MMA monomer, a chemical activator, and optionally a long term storage preservative, and c) a modifier comprising at least a fatty acid or a triglyceride oil and optionally a long term storage preservative and/or a drug.

The kit preferably comprises three separately packed components, a powder phase, a liquid phase, and a modifier according to the present embodiments. Any drug of the kit could be provided in a separate package or be included in the package of the solid, phase, the liquid phase and/or the modifier.

The present embodiments relate to producing an alternative formulation for acrylic bone cements, specifically poly(methyl methacrylate) (PMMA) bone cements, including a fatty acid or a triglyceride oil for controlling the Young's modulus and the drug delivery from the cements. Acrylic bone cements are currently used for prosthesis fixation and as bone fillers in vertebroplasty and kyphoplasty, following tumor resection or other bone augmentation applications. Acrylic bone cements consist of at least five basic components including prepolymerized PMMA beads; methyl methacrylate (MMA) monomer; a radical initiator, such as benzoyl peroxide (BPO); a chemical activator, such as N,N-dimethyl-p-toluidine (DMPT); and a radiopacifier, such as barium sulfate, strontium salt or zirconium dioxide.

Commercial formulations include storage stabilizers, such as hydroquinone. Several alternative formulations also include additives, such as chlorophyll, ethanol and ascorbic acid among others. The chemical activator first decomposes the benzoyl peroxide in order to generate benzoyloxy radicals that attack the vinyl groups in the MMA monomer to initiate the reaction at room temperature. Prepolymerized PMMA beads allow the reaction to proceed faster than if the polymerization was carried out from only the monomer. The prepolymerized beads swell in the presence of the monomer at the same time that the chains propagate until the radicals are consumed and the cement hardens. The radiopacifier is used for visual contrast during the interventional procedure, which is monitored trough fluoroscopy, or for radiographic observation upon surgery.

Commercially available acrylic bone cements consist of a two-phase system:

a) a solid phase consisting of at least the prepolymerized poly(methyl methacrylate) (or its copolymers with styrene or methyl acrylate) beads, a radiopacifier (barium sulphate, strontium salt or zirconium dioxide), and a radical initiator (benzoyl peroxide); and b) a liquid phase consisting of at least methyl methacrylate monomer and a chemical activator (N,N-dimethyl-p-toluidine).

The present embodiments incorporate a fatty acid or a triglyceride oil, which is preferably to be dissolved in the liquid phase. Fatty acids or triglyceride oils can be taken from the following non-limiting list of compounds: myristic acid, palmitic acid, palmitoleic acid, stearic acid, oleic acid, linoleic acid, α-linoleic acid, α-eleostearic acid, ricinoleic acid, vernolic acid, licanic acid, soybean oil, castor oil, palm oil, sunflower oil, linseed oil, paraffin oil, peanut oil, teel oil, boleko oil, mustard oil, olive oil, seneca oil, coconut oil, coffee oil, rapeseed oil, corn oil, cottonseed oil, jojoba oil, macassar oil, neem oil, orris root oil, safflower oil, canola oil, methyl linoleate and tung oil. The liquid phase can be prepared by mixing together at least the following components until a homogeneous solution is obtained:

1. The desired amount(s) of the fatty acid(s) or the triglyceride oil(s) or a mixture thereof, represents non-trace amounts up to 50 vol % of the liquid phase. The preferred amounts would depend on the fatty acid(s) or the triglyceride oil(s) or mixtures of them added to the formulation. For example, if a low porosity cement with a reduction in Young's moduli reduction between 5 and 95% is desired, linoleic acid should be added, preferably from 0.1 to 12 vol % of the liquid phase. Additionally, if a higher porosity cement—with a drug release profile as exemplified in FIG. 10—with a reduction in Young's moduli between 5 and 80% is desired, castor oil should be added, preferably from 0.1 to 20 vol %. Alternatively, a higher porosity cement—with a drug release profile as exemplified in FIG. 10—and with a reduction in Young's moduli between 5 and 70%, can also be achieved by adding oleic acid, preferably from 0.1 to 20 vol %. This alternative gives a higher concentration of released drug.

2. The desired amount(s) of acrylic monomer(s) such as methyl methacrylate, represents from 50 up to 99.9 vol % of the liquid phase.

3. The desired amount of chemical activator such as N,N-dimethyl-p-toluidine, preferably represents from 0.1 up to 10 vol % of the liquid phase and equimolar with the radical initiator in the powder phase.

4. A storage stabilizer, preferably but not limited to hydroquinone, preferably represents from 0.1 up to 0.5 vol % of the liquid phase.

The powder phase can be prepared by mixing together at least the following components until a homogeneous powder is obtained:
1. Prepolymerized poly(methyl methacrylate) (or its copolymers with methyl acrylate or styrene) beads.
2. A radical initiator, preferably but not limited to benzoyl peroxide below 10 wt % of the powder phase, which is preferably equimolar with the chemical activator, N,N-dimethyl-p-toluidine.
3. A radiopacifier, preferably but not limited to barium sulphate, strontium salt or zirconium dioxide.

Active pharmaceutical or biological components (drugs or growth factors) can be added to either the liquid or the powder phase and/or previously dissolved in any of the components, preferably in the fatty acids or the triglyceride oils. The drugs can in an illustrative example be selected from any of the groups of: antibiotics, growth factors, bisphosphonates, anti-inflammatories, painkillers and/or anti-cancer drugs. The release of such drugs from the bone cement may be controlled through the pores promoted by the fatty acids or the triglyceride oils. Some factors controlling the drug release from the material comprise pore size, pore fraction and pore interconnectivity. Controlling these features directly enables the control of the amount and rate of drug release into the body. For example, larger and highly interconnected pores will result in a larger amount of drug released per time unit, while smaller and complicated pore networks would work contrariwise. Antibiotics, such as gentamicin or vancomycin, may be critical to reduce any kind of inflammatory side effects or bacterial infections that may result after e.g. a hip replacement procedure.

Any commercial cement is a potential base cement that can be modified with fatty acids or triglyceride oils. For the preparation of the modified cement, both the liquid and the powder components are mixed during 30 seconds or the time recommended by the manufacturer of the base cement, preferably using a cap mixer or other appropriate mixing devices. The powder is preferably added to the liquid. Depending on the nature of the fatty acid or the triglyceride oil included in the liquid or the powder component or added separately, the properties of the bone cement will be affected via different mechanisms. For example, small amounts of linoleic acid could lead to chemical modification by methacrylation of linoleic acid according to the mechanism shown in FIG. 1.

Accordingly, the present embodiments provide an enhanced acrylic bone cement with the following advantages, depending on the modifier(s) that are used:
1. Mechanocompatibility with cancellous bone due to a lower, tunable Young's modulus with the possibility to be adapted to different levels of osteoporosis. Mechanocompatibility can be achieved by:
   a. Chemical modification: copolymerization and/or grafting of unsaturated fatty acids or triglyceride oils and PMMA.
   b. Physical modification: unreacted fatty acids or triglyceride oils acting as plasticizers.
   c. Introduction of pores into the microstructure.
2. Enhanced osseointegration, when pores are introduced, due to supported osteoblast differentiation and new tissue ease-of-penetration into the material.
3. Enhanced controllable drug delivery properties, when pores are introduced, due to their acting as drug reservoirs. The fatty acids and the triglyceride oils may also act as drug carriers.

The present embodiments provide a wide range of compositions that can be achieved mainly by changing the following variables:
1. The concentration(s) of the fatty acid(s) or the triglyceride oil(s) or a mixture of them, preferably below 50 vol % of the liquid phase.
2. The type of fatty acid or triglyceride oil.
3. The liquid-to-powder ratio between the liquid and powder component, preferably in the range of 0.3-0.9 mL/g.
4. The radiopacifier, preferably in the range of 10-45 wt % of the powder phase.
5. The concentration of radical initiator (preferably in the range of 0.5-10 wt %) or the concentration of chemical activator, which should preferably be equimolar to the concentration of radical initiator.

The amounts and type of modifiers in the above listing are to be chosen depending on the desired properties of the acrylic cement. For example, if low porosity is desired together with a very low Young's modulus, small amounts of e.g. linoleic acid (0.5-12 vol %) are suitable, whereas if a high porosity is desired, together with a medium to low Young's modulus, medium amounts of e.g. castor oil (10-18 vol %) can be used. Accordingly, a wide range of low Young's modulus drug-delivering injectable acrylic cements can be produced to fit the specific needs of each patient.

The present embodiments will provide enhanced performance to current applications of acrylic bone cements such as, but not limited to:
1. Hip arthroplasty
2. Knee arthroplasty
3. Small joint arthroplasty
4. Dental implantology
5. Percutaneous vertebral augmentation, including kyphoplasty and vertebroplasty
6. Femeroplasty
7. Treatment of metastatic spinal disease
8. Prosthetic fixation
9. Screw augmentation
10. Sacroplasty
11. Bone substitution
12. Infection treatment, including antibiotic containing beads and/or spacers
13. Drug release
14. Cranioplasty
15. Plastic surgery application, including reconstruction of functionality and esthetic appearance.
16. Maxillofacial surgery
17. Bone augmentation
18. Fracture healing
19. Fusion
20. Disc replacement
21. Bleeding management, including treatment of disorders and acute interventions
22. Cartilage repair
23. Oncological treatment, including radiotherapy, chemotherapy and reconstruction of tissue and functionality after surgery.
24. Further cemented surgeries The present embodiments further comprise a kit for commercializing the cement. The kit comprises three separately packed components. The liquid component contains appropriate amounts of the monomer, a chemical activator, and a storage stabilizer. The powder component contains appropriate amounts of the polymer, a radical initiator and a radiopacifier. The modifier component contains appropriate amounts of fatty acids or triglyceride oils and a storage stabilizer, Drugs may additionally be incorporated into any of the components.

An aspect of the embodiments relates to an injectable composition for a bone cement material comprising a dry powder component, a liquid component and a modifier configured to modify a Young's modulus of the bone cement material. The modifier is linoleic acid or a derivative thereof, and is present in a concentration of 0.1 to 12 v/v of the liquid component.

In an embodiment, the modifier is present in a concentration of 0.5 to 12 v/v (vol %) of the liquid component. In a preferred embodiment, the modifier is present in a concentration of 1 to 10 v/v of the liquid component, preferably 2 to 10 v/v of the liquid component and more preferably 2 to 6 v/v of the liquid component.

In an embodiment, the modifier is present in a concentration of 0.1 to 3 w/w (wt %) of total bone cement material. In a preferred embodiment, the modifier is present in a concentration of 0.25 to 3 w/w of the total bone cement material, preferably 0.25 to 2.5 w/w of the total bone cement material, and more preferably 0.5 to 2.5 w/w of the total bone cement material, such as 0.5 to 1.5 w/w of the total bone cement material.

In an embodiment, the modifier consists of pure linoleic acid, or a pure derivative thereof. Hence, in a particular embodiment the modifier is not provided in the form of a general oil or a mixture of fatty acids or triglycerides but is rather provided as pure linoleic acid, or a pure derivative thereof. Pure as referred herein implies that the modifier consists of at least 90 w/w linoleic acid (or derivative thereof), preferably at least 95 w/w, more preferably at least 96 w/w, at least 97 w/w, at least 98 w/w and at least 99 w/w linoleic acid (or derivative thereof).

In an embodiment, the modifier is present in the liquid component. Hence, the modifier is preferably admixed to the liquid component to form a homogenous solution, which is then mixed with the dry powder component.

In an embodiment, the liquid component comprises methyl methacrylate (MMA) monomer and the dry powder component comprises prepolymerized poly(methyl methacrylate) (PMMA) or a copolymer of PMMA and a pharmaceutically acceptable polymer, preferably a copolymer of PMMA and polystyrene.

In an embodiment, the injectable composition further comprises a radical initiator, preferably benzoyl peroxide (BPO), and a chemical activator, preferably N,N-dimethyl-p-toluidine (DMPT).

In an embodiment, the radical initiator is present in a concentration of 0.1-20 wt % of the dry powder component, preferably 0.5-10 wt % of the dry powder component.

In an embodiment, the injectable composition further comprises a radiocontrast agent. In a particular embodiment, radiocontrast agent is selected from barium sulfate, zirconium dioxide, a strontium salt, an ionic or non-ionic iodine-based compound, or a combination thereof. In another particular embodiment, the radiocontrast agent is present in a concentration of 1-90 wt % of the dry powder component, preferably 5-60 wt % or 10-55 wt %, more preferably 25-50 wt %, such as 29 wt % or 45 wt % of the dry powder component.

In an embodiment, the injectable composition further comprises a pharmaceutically active agent. In a particular embodiment, the pharmaceutically active agent is an antibiotic or a mixture of at least two antibiotics. Further examples of pharmaceutically active agents that can be used instead of or as a complement to antibiotics include a growth factor, a bisphosphonate, an anti-inflammatory agent, an analgesic agent and/or a cytotoxic agent. Further pharmaceutically active agents that can be used include antiphlogistic agents, steroids and hormones.

According to a particularly preferred embodiment, the at least one pharmaceutical agent is an antibiotic. Preferably, the at least one antibiotic is selected from the group consisting of aminoglyoside antibiotics, glycopeptide antibiotics, lincosamide antibiotics, gyrase inhibitors, carbapenems, cyclic lipopeptides, glycylcyclines, oxazolidones, and polypeptide antibiotics. According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, timidazole, omidazole, and colistin, as well as salts and esters thereof. Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

In an embodiment, the antibiotic is vancomycin, tobramycin and/or gentamycin.

In an embodiment, the antibiotic is present in a concentration of 1 to 10 wt % of the dry powder component.

In an embodiment, the antiphlogistic agent is preferably selected from the group consisting of non-steroidal antiphlogistic agents and glucocorticoids. According to a particularly preferred embodiment, the antiphlogistic agent is selected from the group consisting of acetylsalicylic acid, ibuprofen, diclofenac, ketoprofen, dexamethasone, prednisone, hydrocortisone, hydrocortisone acetate, and fluticasone.

In an embodiment, the analgesic agent selected from the group consisting of paracetamol (known in the U.S. as acetaminophen or simply APAP), non-steroidal anti-inflammatory drugs (NSAIDs) such as the salicylates, and opioid drugs such as morphine and oxycodone. Further examples include lidocaine (INN), also referred to as xylocaine, or lignocaine, which is a common local anesthetic and antiarrhythmic drug.

In an embodiment, the hormone is preferably selected from the group consisting of serotonin, somatotropin, testosterone, estrogen, parathyroid hormone (PTH), parathormone and parathyrin.

In an embodiment, the growth factor is selected from the group consisting of fibroblast growth factor (FGF), transforming growth factor (TGF), platelet derived growth factor (PDGF), epidermal growth factor (EGF), vascular endothelial growth factor (VEGF), insulin-like growth factors (IGF), hepatocyte growth factor (HGF), bone morphogenetic protein (BMP), transforming growth factor-β1, interleukin-1B, interleukin 8, and nerve growth factor.

In an embodiment, the cytostatic agent is preferably selected from the group consisting of alkylating agents, platinum analogues, intercalating agents, mitosis inhibitors, taxanes, topoisomerase inhibitors, and antimetabolites.

In an embodiment, the bisphosphonate is preferably selected from the group consisting of zoledronate and alendronate.

In an embodiment, the dry powder component has a particle size of 10-1000 μm, preferably 50-300 μm.

In an embodiment, the injectable composition has a liquid-to-powder ratio between the liquid component and the dry powder component in a range of 0.1-1.5 mL/g, preferably 0.3-0.9 mL/g.

In an embodiment, the injectable composition further comprises a radiocontrast agent at a concentration of 5 to 60 wt % of the dry powder component.

Another aspect of the embodiments relates to a bone cement obtainable by mixing a liquid component comprising i) methyl methacrylate (MMA) monomer and a chemical activator, preferably N,N-dimethyl-p-toluidine, with a modifier in terms of linoleic acid or a derivative thereof, present in a concentration of 0.1 to 12 v/v of the liquid component to form a homogenous solution. The homogenous solution is then mixed with a dry powder component comprising i) prepolymerized poly(methyl methacrylate) (PMMA) or a copolymer of PMMA and a pharmaceutically acceptable polymer, preferably a copolymer of PMMA and polystyrene, ii) a radical initiator, preferably benzoyl peroxide, and iii) optionally a radiocontrast agent, preferably barium sulfate, strontium salt or zirconium dioxide, to form the bone cement.

In an embodiment, the bone cement is obtainable by the further step setting a mixture of the homogenous solution with the dry powder component at a setting reaction temperature equal to or below 45° C., preferably equal to or below 42° C. and more preferably equal to or below 37° C.

In an embodiment, the bone cement has a Young's modulus within a range of 2 to 40% of a Young's modulus of a control bone cement comprising the liquid component and the dry powder component but lacking the modifier, preferably within a range of 2 to 30% of the Young's modulus of the control bone cement, more preferably within a range of 5 to 25% of the Young's modulus of the control bone cement.

A further aspect of the embodiments relates to a method of producing an injectable composition for a bone cement material. The method comprises mixing a dry powder component, a liquid component and a modifier to form the bone cement material. The modifier is linoleic acid or a derivative thereof, and is present in a concentration of 0.1 to 12 v/v of the liquid component.

In an embodiment, the method comprises mixing the liquid component and the modifier to form a homogenous solution. The homogenous solution is then mixed with the dry powder component to form the bone cement material.

Yet another aspect of the embodiments relates to the use of a modifier at a concentration of 0.1 to 12 w/w of a liquid component of a bone cement material to modify Young's modulus of the bone cement material formed by mixing the liquid component, the modifier and a dry powder component. The modifier is linoleic acid or a derivative thereof.

A further aspect of the embodiments relates to use of an injectable composition for a bone cement material according to above or a bone cement according to above in a medical application selected from a group consisting of hip arthroplasty, knee arthroplasty, small joint arthroplasty, dental implantology, percutaneous vertebral augmentation, such as kyphoplasty or vertebroplasty, femeroplasty, treatment of metastatic spinal disease, prosthetic fixation, screw augmentation, sacroplasty, bone substitution, cranioplasty, plastic surgery application, maxillofacial surgery, bone augmentation, fracture healing, disc replacement, cartilage repair, oncological treatment, and cemented surgeries.

A further aspect of the embodiments relates to a kit for producing an injectable composition for a bone cement material. The kit comprises a container comprising a liquid component and a container comprising a modifier in terms of linoleic acid or a derivative thereof at an amount corresponding to a concentration of 0.1 to 12 v/v of the liquid component when mixing the modifier and the liquid component. The kit also comprises a container comprising a dry powder component. The kit further comprises instructions for mixing the modifier and the liquid component to form a homogenous solution and instructions for mixing the dry powder component and the homogenous solution to form the injectable composition for the bone cement material.

The containers of the kit can be any ampoule, phial, container, vessel or chamber containing the constituents and ingredients of the bone cement material. Mixing of the liquid component and the modifier and mixing the homogenous solution and the dry component can take place in any of the containers of the kit or in one or more other mixing containers.

The liquid component, dry powder component and modifier are preferably sterilized prior to packaging into the respective container. Sterilization can be performed according to techniques well known in the art. For instance, sterilization of the modifier linoleic acid can be performed by sterilization filtering.

Yet another aspect of the embodiments relates to a method of producing a subject-specific injectable composition for a bone cement material. The method comprises determining a target Young's modulus of the bone cement material based on a bone mineral density of a subject. The method also comprises determining a concentration of a modifier within a range of 0.1 to 12 v/v of a liquid component based on the target Young's modulus. The method further comprises mixing a dry powder component, the liquid component and the modifier to form the bone cement material. In an embodiment, the modifier is linoleic acid or a derivative thereof and is present in the determined concentration.

Bone mineral density (BMD), also referred to as bone density, is a medical term normally referring to the amount of mineral matter per square centimeter of bones. BMD is typically measured by a procedure called densitometry, often performed in the radiology or nuclear medicine departments of hospitals or clinics. The measurement is painless and non-invasive and involves low radiation exposure. Measurements are most commonly made over the lumbar spine and over the upper part of the hip. The forearm or wrist may be scanned if the hip and lumbar spine are not accessible.

Non-limiting but illustrative examples of BMD tests that can be used according to the embodiments include dual-energy X-ray absorptiometry (DXA or DEXA), quantitative computed tomography (QCT), qualitative ultrasound (QUS), single photon absorptiometry (SPA), dual photon absorptiometry (DPA), digital X-ray radiogrammetry (DXR) and single energy X-ray absorptiometry (SEXA).

Once the BMD of the subject is available a target Young's modulus of the bone cement material can be determined. Hence, the Young's modulus of the bone cement material to be injected into the subject is determined to be adapted to the determined BMD of the particular subject. For instance, a subject having lower BMD than average would not benefit from receiving a bone cement material with very high Young's modulus since then the problems discussed in the background section, including promoting fractures, could occur. Hence, in an embodiment the Young's modulus of the bone cement material is tailored to be optimized or at least adapted to the characteristics of the bone in the subject such as preferably represented by the determined BMD value.

Once the target Young's modulus has been determined, preferably based on the BMD of the subject, the concentration or amount of a modifier to be included in the bone cement material is determined in order to achieve a bone cement material having the target Young's modulus. This determination of the concentration of modifier in the bone cement material is preferably determined based on the target Young's modulus and a control Young's modulus for the bone cement material.

The control Young's modulus for the bone cement material is the Young's modulus of the bone cement material without any added modifier. Hence, this control Young's modulus represents the value obtained for the bone cement material with the use of any modifier.

In a particular embodiment, the determination of the concentration of the modifier is performed based on a look-up table or diagram listing Young's modulus values for the bone cement material at different concentrations of the modifier. Alternatively, a function, look-up table or other data set that outputs a reduction in the Young's modulus of the bone cement value based on an input concentration of the modifier. For instance, a table or diagram as shown in Table 6 or 7 or FIG. 5 could be used to determine the concentration of the modifier based on the target Young's modulus.

Thus, in an embodiment the look-up table, diagram or function or other data set that is used to convert target Young's modulus into concentrations of the modifier is typically generated based on the control Young's modulus of the bone cement material and experiments in which Young's modulus of various bone cement materials with different concentrations of the modifier have been determined.

Once the concentration of the modifier has been determined the bone cement material is produced by mixing the liquid component, the modifier and the dry powder component as described herein and where the modifier is included in the determined concentration.

Although BMD is a preferred parameter to monitor bone characteristics of a subject and tailor a bone cement other parameters that are representative of bone characteristics of a subject, such as bone strength could be used. For instance, apparent bone trabecular volume (BV/TV) is such a parameter that could be used according to the embodiments instead of or as a complement to BMD.

A derivative of linoleic acid is preferably a salt, an ester or a conjugate of linoleic acid and more preferably a pharmaceutically acceptable salt or ester of linoleic acid. Non-limiting but preferred examples of such salts, esters and conjugates of linoleic acid include methyl linoleate, ethyl linoleate, potassium linoleate, sodium linoleate, linoleic acid sodium salt, conjugated linoleic acid, conjugated methyl ester linoleic acid, conjugated ethyl ester linoleic acid.

Embodiments of the present invention have been compared to the bone cement disclosed in Lam et al. 2010. The results of the comparison is presented in Table 1 below using a PMMA bone cement for arthroplasty (Simplex P):

TABLE 1

Comparison of bone cement of Lam et al. 2010 and an embodiment

|  | Lam et al. 2010 | LA in PMMA cement for arthroplasty |
|---|---|---|
| w/w of total bone cement | 3.4 | 2.8 |
| v/v of liquid component | 15 | 8.9 |
| w/w of dry powder component | 4.5 | 4 |
| E modulus (MPa) | 774 | 88 |

TABLE 1-continued

Comparison of bone cement of Lam et al. 2010 and an embodiment

|  | Lam et al. 2010 | LA in PMMA cement for arthroplasty |
|---|---|---|
| Compressive strength (MPa) | 49 | 2.6 |
| E modulus (% of control cement) | 43.4 | 5.4 |
| Compressive strength (% of control cement) | 84.5 | 3.2 |

Thus, the present embodiment using a significant lower concentration of linoleic acid in the liquid component as compared to Lam et al. 2010 provides a significant reduction in E modulus and compressive strength as compared to the control bone cement (without any added linoleic acid). The bone cement of the embodiments additionally does not suffer from poor cell viability due to unconverted monomers as does the bone cement disclosed in Lam et al. 2010.

The reduction of Young's modulus achieved by the embodiment was significantly different from the one obtained by Lam et al. 2010, i.e. 88 MPa and 774 MPa, respectively, using only about half the amount of linoleic acid in the liquid component as compared to Lam et al. 2010. This result was surprising and unexpected.

The experiment was repeated with several other cement systems, in addition to the PMMA cement for arthroplasty (Simplex P), to verify the findings. The results clearly show that the modifier linoleic acid in the concentration ranges of the present embodiments has much stronger effect on the mechanical properties of the bone cement than presented in Lam et al. 2010. The bone cements presented in Table 2 are two different PMMA cements intended for vertebral augmentation or vertebroplasty (denoted PMMA cement for vertebral augmentation cement or vertebroplasty 1 (Osteopal V) and PMMA cement for vertebral augmentation cement or vertebroplasty 2 (Opacity+) in the table).

TABLE 2

Mechanical properties of commercial bone cement systems for vertebral augmentation or vertebroplasty with added linoleic acid (LA)

|  | LA in PMMA cement for vertebral augmentation or vertebroplasty 1 | | LA in PMMA cement for vertebral augmentation or vertebroplasty 2 | |
|---|---|---|---|---|
| w/w of total bone cement | 1.45 | 2.5 | 1.0 | 1.5 |
| v/v of liquid component | 5.7 | 10 | 4.1 | 6.1 |
| w/w of dry powder component | 2 | 3.5 | 1.3 | 2 |
| E modulus (MPa) | 400 | 201 | 320.4 | 75.6 |
| Compressive strength (MPa) | 18.7 | 11.6 | 7.1 | 1.6 |
| E modulus (% of control cement) | 21.5 | 10.8 | 22.5 | 5.3 |
| Compressive strength (% of control cement) | 28.3 | 17.6 | 10.2 | 2.3 |

Further aspects of the embodiments relates to injectable compositions for a bone cement material, bone cements, methods and kits of producing injectable compositions, uses of a modifier, uses of injectable compositions or bone cements and methods of producing subject-specific injection compositions as described herein but using other unsaturated fatty acids, triglyceride oils or mixtures thereof as modifier instead of linoleic acid and derivatives thereof. In such a case, the concentrations of such an unsaturated fatty acid or triglyceride oil as modifier in the injectable composition or bone cement are as defined in herein and in particular in the following Examples section.

For instance, castor oil, oleic acid, linseed oil, tung oil, ricinoleic acid or a mixture thereof or a mixture of any of these oils and linoleic acid can be used as modifier as disclosed herein. In such a case, castor oil is preferably used as a modifier in a concentration of 3.6-13.7 wt % of the bone cement (12.7-43 v/v of the liquid component), preferably 8.4-13.7 wt % of the bone cement (28.1-43 v/v of the liquid component). Correspondingly, oleic acid is preferably added as modifier in a concentration of 3.6-12.8 wt % of the bone cement (13.5-42.8 v/v of the liquid component), preferably 8.4-12.8 wt % of the bone cement (29.7-42.8 v/v of the liquid component). If linseed oil is used as modifier, linseed oil is preferably used in a concentration of 0.4-5.7 wt % of the bone cement (1.4-20.2 v/v of the liquid component), preferably 0.7-5.7 wt % of the bone cement (2.9-20.2 v/v of the liquid component). Tung oil as modifier is preferably used in a concentration of 0.7-2.2 wt % of the bone cement (2.7-8.2 v/v of the liquid component), preferably 0.7-1.5 wt % of the bone cement (2.7-5.6 v/v of the liquid component). Correspondingly, ricinoleic acid can be used as modifier in a concentration of 3.6-19.4 wt % of the bone cement (12.8-54.8 v/v of the liquid component), preferably 7.1-19.4 wt % of the bone cement (24.6-54.8 v/v of the liquid component).

EXAMPLES

Most of the examples presented herein were prepared by modifying a commercial bone cement formulation whose composition is shown in Table 1. The microstructure of PMMA cement intended for vertebral augmentation or vertebroplasty (Osteopal V) is also shown in FIG. 2. Some examples contain data on modified formulations of PMMA cement intended for arthroplasty (Simplex P) or PMMA cement intended for vertebral augmentation or vertebroplasty (Opacity+), as specified.

TABLE 3

Composition of the commercial formulation (Osteopal V) used in the examples 1-6, 8. The recommended liquid-to-powder ratio is 0.385 mL/g according to the supplier.

|  | wt % |
| --- | --- |
| Powder component | |
| Poly(methyl acrylate-co-methyl methacrylate) | 54.6 |
| Benzoyl Peroxide | 0.4 |
| Zirconium dioxide | 45.0 |
| Chlorophyll | Not specified |
| Liquid component | |
| Methyl methacrylate | 92 |
| N,N-dimethyl-p-toluidine | 2 |
| Other (hydroquinone, chlorophyll) | 6 |

Example 1. Preparation of Porous Injectable Bone Cements Modified with Castor Oil with Various Young's Moduli A commercial bone cement formulation (Table 3) was used to which different amounts of castor oil were added to the liquid component according to Table 4 and 5 until a homogeneous solution was achieved. Extra DMPT was also added to compensate upon removing part of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves.

TABLE 4

Castor oil formulations giving a wide range of Young's moduli. The powder and the liquid refer to the components in Table 3. The liquid-to-powder ratio is not fixed and increases with the amount of castor oil. The underlined values refer to the unmodified commercial formulation.

| Powder (g) | Castor oil (g) | Liquid (μL) | DMPT (μL) | Young's modulus (MPa) | Strength (MPa) | # Specimens tested |
| --- | --- | --- | --- | --- | --- | --- |
| <u>10.0</u> | <u>0.00</u> | <u>3846</u> | <u>0</u> | <u>1862 ± 76</u> | <u>66 ± 2</u> | <u>18</u> |
| 10.0 | 0.50 | 3565 | 6 | 1585 ± 75 | 69 ± 4 | 6 |
| 10.0 | 1.10 | 3227 | 13 | 1114 ± 43 | 43 ± 4 | 6 |
| 10.0 | 1.19 | 3177 | 14 | 929 ± 118 | N/A | 11 |
| 10.0 | 1.50 | 3002 | 18 | 741 ± 88 | 25 ± 3 | 5 |
| 10.0 | 1.85 | 2805 | 22 | 414 ± 69 | 13 ± 2 | 8 |
| 10.0 | 1.88 | 2789 | 22 | 414 ± 89 | 14 ± 2 | 6 |
| 10.0 | 2.00 | 2721 | 24 | 309 ± 47 | 10 ± 1 | 5 |

Figure 3:
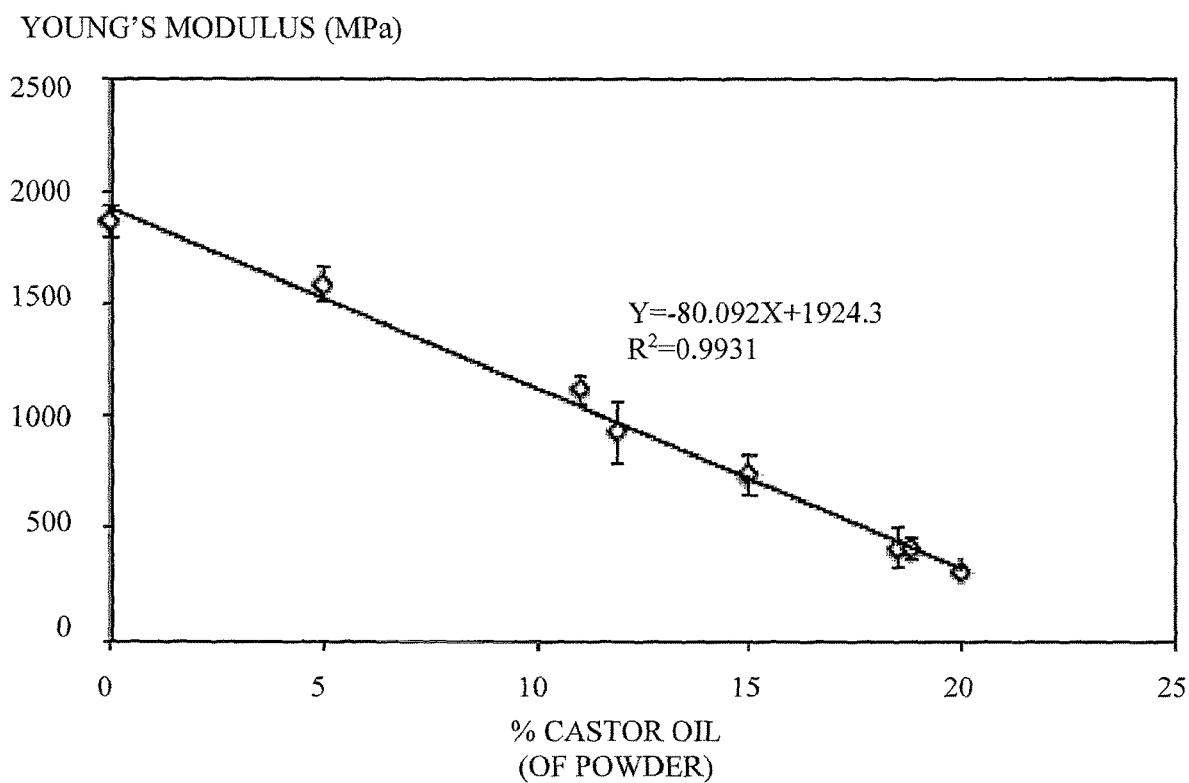
FIG. 3 is a diagram illustrating linear variation of the Young's modulus with the concentration of castor oil.
Figure 4:
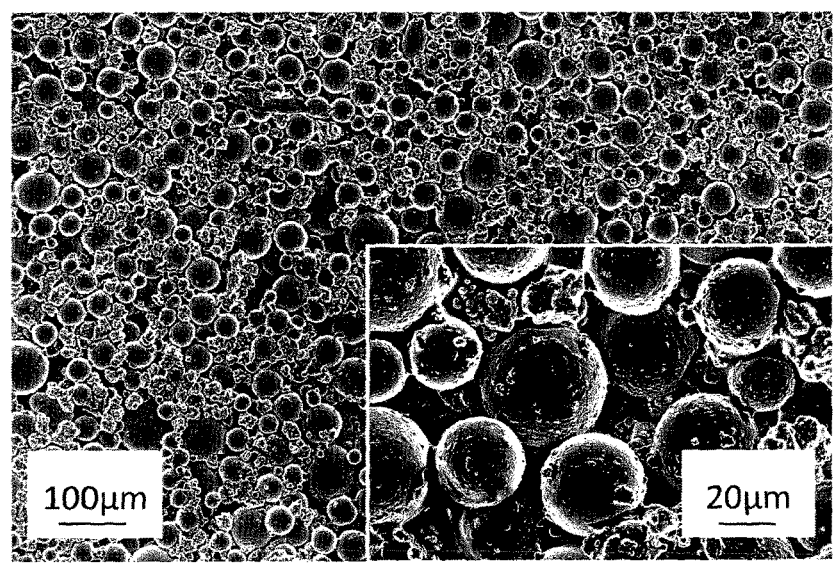
FIG. 4 is a scanning electron micrograph of 17.8% (E≈500 MPa) castor oil containing bone cement (300 and 2000×) showing interconnected porosity in between the polymer beads.

The linear relationship between the concentration of castor oil and the Young's modulus is depicted in FIG. 3, which can be used to select the most appropriate formulation for a certain patient according to the present embodiments. FIG. 4 shows interconnected porosity in between the polymer beads for a castor oil containing bone cement.

TABLE 5

Castor oil formulations giving a wide range of Young's moduli. The powder and the liquid refer to the components in Table 3.

| Castor oil [wt %] | 3.61 (n = 6) | 7.78 (n = 6) | 10.47 (n = 5) | 12.77 (n = 8) | 13.74 (n = 5) |
| --- | --- | --- | --- | --- | --- |
| E [MPa] | 1673 ± 65 | 1190 ± 35 | 786 ± 87 | 429 ± 72 | 361 ± 38 |
| $\sigma_{2\%}$ [MPa] | 68.8 ± 3.6 | 38.4 ± 1.6 | 23.8 ± 2.3 | 12.6 ± 2.5 | 10.0 ± 1.4 |
| $\sigma_u$ [MPa] | 68.8 ± 3.5 | 42.9 ± 3.7 | 24.6 ± 2.5 | 12.8 ± 2.4 | 10.3 ± 1.1 |

Example 2. Preparation of Low-Porosity Injectable Bone Cements Modified with Linoleic Acid with Various Young's Moduli A commercial bone cement formulation (Table 3) was used to which different amounts of linoleic acid were added to the liquid component according to Table 6 until a homogeneous solution was achieved. In this example, the amounts of linoleic acid required to obtain a wide range of Young's moduli were relatively small. Therefore, DMPT compensation was omitted. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves.

TABLE 6

Linoleic acid formulations giving a wide range of Young's moduli.
The powder and the liquid refer to the components in Table 3.
The liquid-to-powder ratio is fixed to 0.385 mL/g. The underlined
values refer to the unmodified commercial formulation.

| Powder (g) | Linoleic acid (µL) | Liquid (µL) | Young's modulus (MPa) | Strength (MPa) | # Specimens tested |
|---|---|---|---|---|---|
| <u>10.0</u> | <u>0</u> | <u>3846</u> | <u>1862 ± 76</u> | <u>66 ± 2</u> | <u>18</u> |
| 10.0 | 15 | 3831 | 1781 ± 52 | 78 ± 1 | 9 |
| 10.0 | 38 | 3808 | 1576 ± 107 | 69 ± 2 | 6 |
| 10.0 | 75 | 3771 | 917 ± 74 | 25 ± 1 | 9 |
| 10.0 | 113 | 3732 | 531 ± 40 | 18 ± 5 | 9 |
| 10.0 | 151 | 3695 | 47 ± 3 | N/A | 13 |

Figure 5:
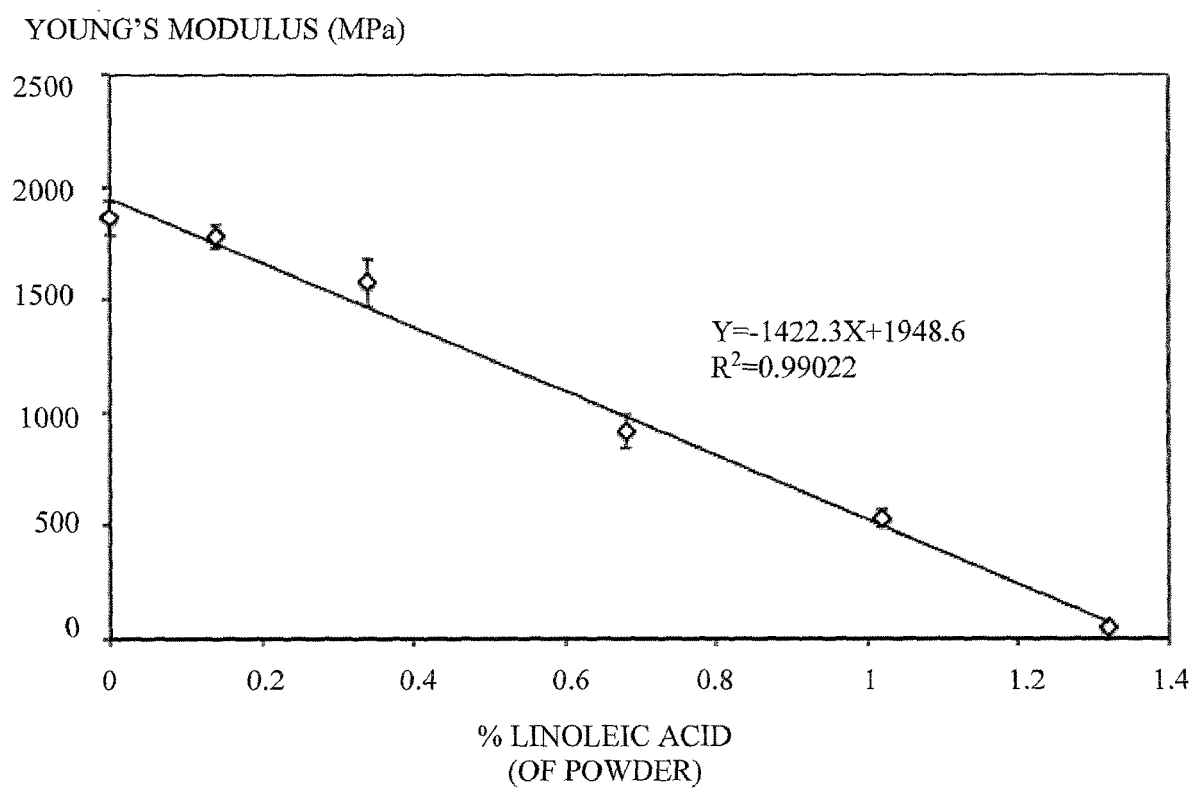
FIG. 5 is a diagram illustrating linear variation of the Young's modulus with the concentration of linoleic acid.

The linear relationship between the concentration of linoleic and the Young's modulus is depicted in FIG. 5, which can be used to select the most appropriate formulation for a certain patient according to the present embodiments. No significant differences in mechanical properties were observed when adding the linoleic acid to the liquid or the powder for 1.36 or 6.8 vol % linoleic acid (correspond to 0.35 or 1.73 w/w of the bone cement). The concentrations of linoleic acid presented in FIG. 5 can be converted into w/w of the total bone cement by a multiplication factor of 0.735 and into v/v of the liquid phase by a multiplication factor of 2.886. Hence, concentrations of linoleic acid in FIG. 5 extends from about 0.09 to about 0.98 w/w of the total cement, and in more detail about 0.09, 0.19, 0.53, 0.73 and 0.98 w/w of the total cement).

TABLE 7

Linoleic acid formulations giving a wide range of Young's moduli.
The powder and the liquid refer to the components in Table 3.

| | Linoleic acid (wt % of total) | | | | |
|---|---|---|---|---|---|
| | 0 (n = 27) | 0.25 (n = 6) | 0.50 (n = 6) | 0.75 (n = 6) | 1.00 (n = 6) |
| Linoleic acid (vol % of liquid) | 0 | 1 | 2 | 3 | 4 |
| E [MPa] | 1690 ± 69 | 1610 ± 173 | 1486 ± 52 | 1047 ± 61 | 611 ± 36 |
| $\sigma_{2\%}$ [MPa] | 71.2 ± 6.5 | 66.7 ± 3.5 | 52.3 ± 1.6 | 27.0 ± 0.7 | 15.5 ± 0.7 |
| $\sigma_u$ [MPa] | 71.2 ± 6.5 | 66.7 ± 3.5 | 52.9 ± 1.6 | 27.2 ± 0.7 | 17.0 ± 1.5 |

Figure 6:
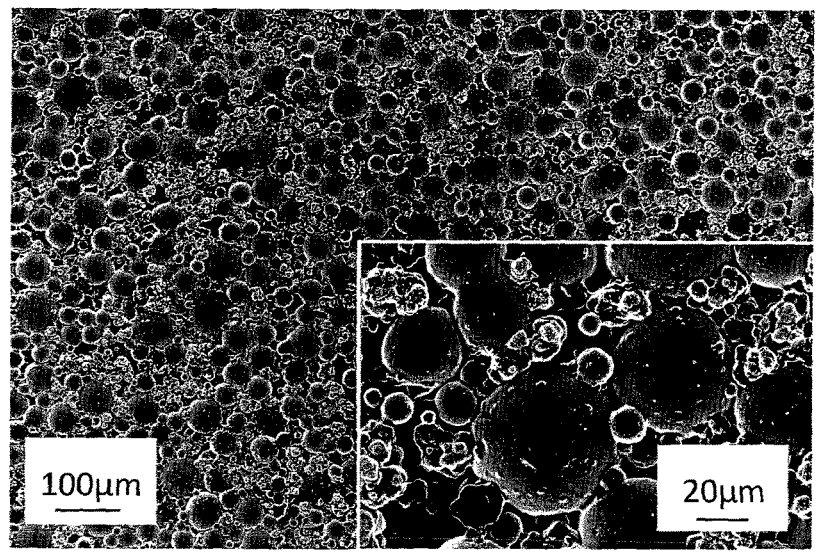
FIG. 6 is a scanning electron micrograph of 1.02% (E≈500 MPa) linoleic acid containing bone cement (300 and 2000×) showing interconnected porosity in between the polymer beads.

FIG. 6 illustrates the interconnected porosity in between the polymer beads for linoleic acid containing bone cement.

Figure 7:
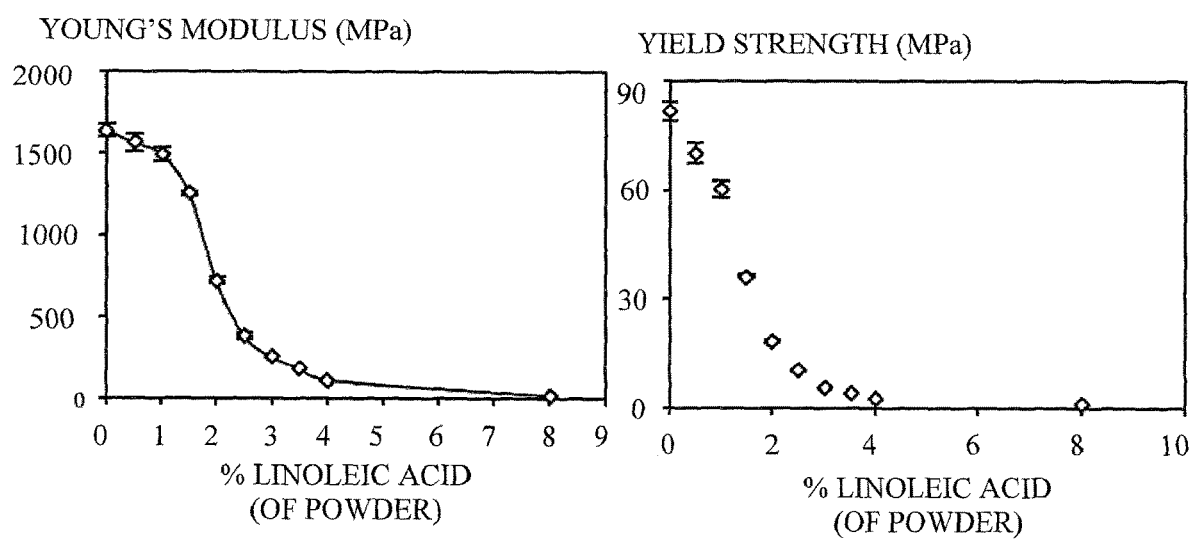
FIG. 7 shows diagrams illustrating Young's modulus and yield strength of PMMA bone cement Simplex P modified with linoleic acid.

Commercial formulation Simplex P was also modified with linoleic acid, showing the potential for tailoring the mechanical properties of also this cement, see FIG. 7. The concentrations of linoleic acid presented in FIG. 7 can be converted into w/w of the total bone cement by a multiplication factor of 0.68. Hence, the largest linoleic acid concentration tested in FIG. 7 was about 5.4 w/w of the total cement, corresponding to 18 v/v of the liquid component.

Figure 8:
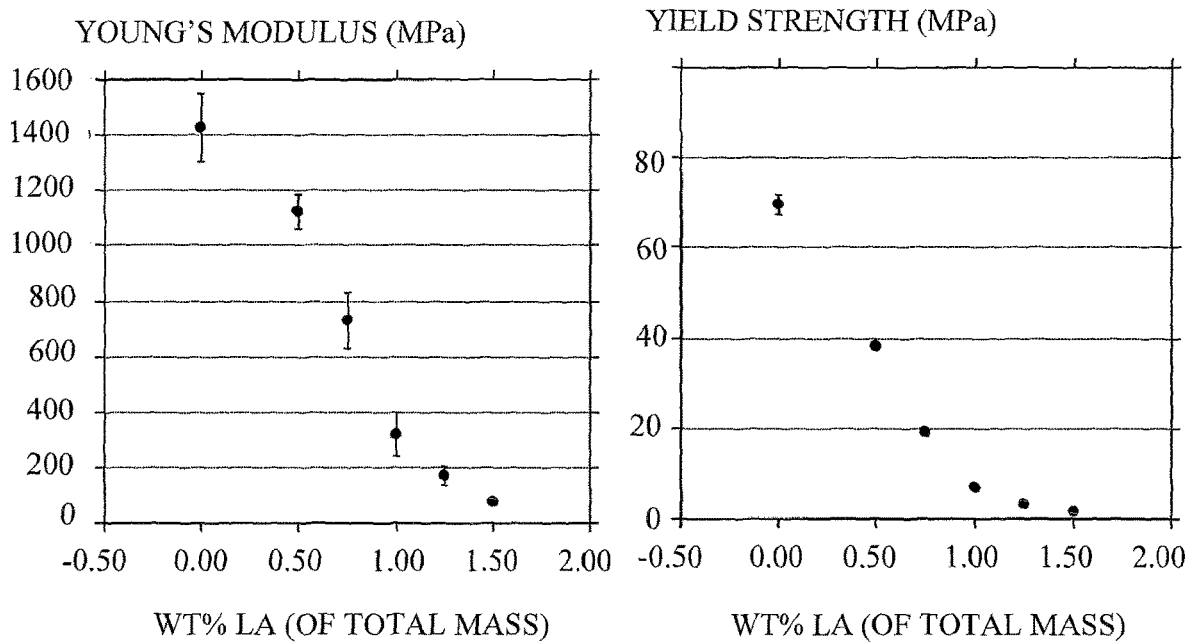
FIG. 8 shows diagram illustrating mechanical properties of commercial formulation Opacity+ modified with different amounts of linoleic acid.

Commercial formulation Opacity+ was also modified with linoleic acid, showing the potential for tailoring the mechanical properties of also this cement, see FIG. 8. Here the largest linoleic acid concentration tested was 1 w/w of the total cement, corresponding to 4.1 v/v of the liquid component.

Example 3. Preparation of Porous Injectable Bone Cements Modified with Oleic Acid with Specific Young's Moduli of 800 and 400 MPa A commercial bone cement formulation (Table 3) was used to which two amounts of oleic acid were added to the liquid component according to Table 8 until a homogeneous solution was achieved. Extra DMPT was also added to compensate upon removing part of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves.

TABLE 8

Oleic acid formulations giving Young's moduli of 800 and
400 MPa. The powder and the liquid refer to the components
in Table 3. The liquid-to-powder ratio is not fixed and
increases with the amount of castor oil. The underlined
values refer to the unmodified commercial formulation.

| Powder (g) | Oleic acid (g) | Liquid (µL) | DMPT (µL) | Young's modulus (MPa) | Strength (MPa) | # Specimens tested |
|---|---|---|---|---|---|---|
| <u>10.0</u> | <u>0.00</u> | <u>3846</u> | <u>0</u> | <u>1862 ± 76</u> | <u>66 ± 2</u> | <u>18</u> |
| 10.0 | 1.19 | 3128 | 15 | 834 ± 123 | 40 ± 3 | 6 |
| 10.0 | 1.85 | 2730 | 23 | 483 ± 107 | 16 ± 6 | 4 |

Figure 9:
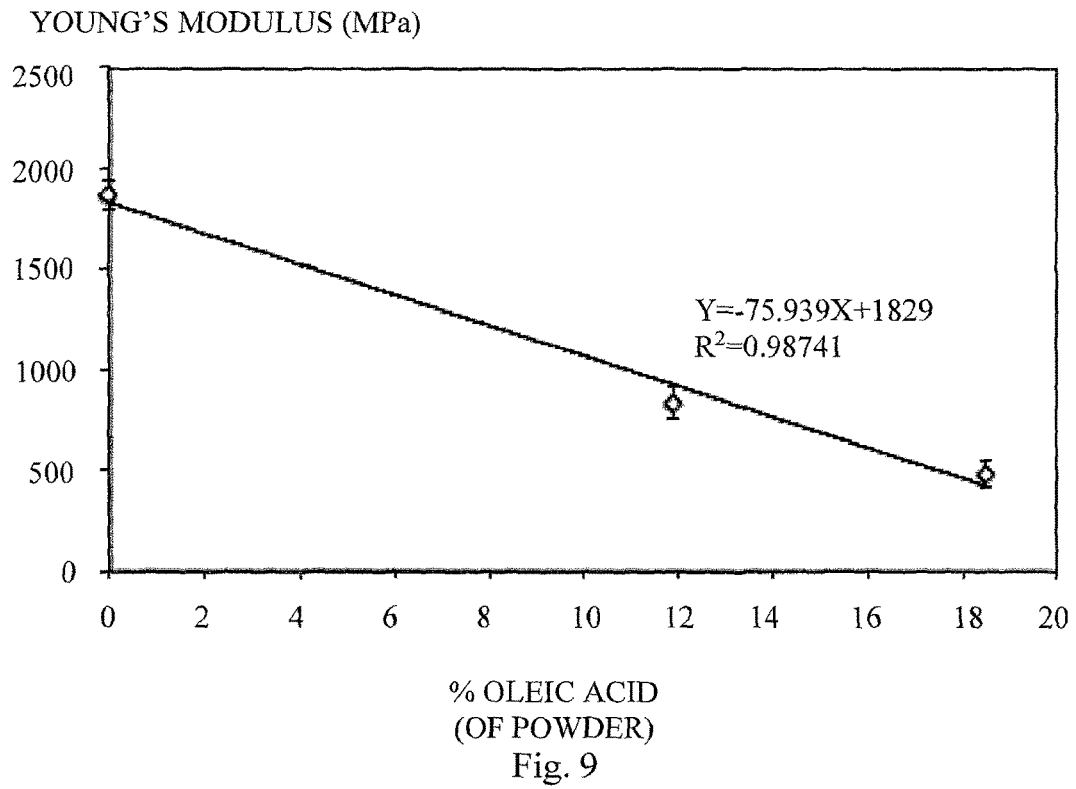
FIG. 9 is a diagram illustrating linear variation of the Young's modulus with the concentration of oleic acid.

The linear relationship between the concentration of oleic acid and the Young's modulus is depicted in FIG. 9, which can be used to select the most appropriate formulation for a certain patient.

Example 4. Antibiotic Release Study from Bone Cements Modified with Castor Oil, Linoleic Acid and Oleic Acid An antibiotic release study was done for specimens containing Vancomycin (2.40 wt % of the powder; approximately 1.76 wt % of the total material) for a total of 1 week. Vancomycin was loaded by mixing it in the powder component according to the formulations in Table 9 and the cements were prepared according to the present embodiments. Five specimens were tested per formulation. The specimens were cylindrical with a diameter of 6 mm and a thickness of 3 mm. The release was carried out in 3 mL PBS at 37° C. without stirring and the medium was replaced at every time point by fresh pre-heated (37° C.) medium. The release of vancomycin was studied by UV-VIS spectrophotometry at a wavelength of 280 nm.

TABLE 9

Vancomycin containing formulations

| | Formulation | | | | |
|---|---|---|---|---|---|
| | Powder (g) | Vancomycin (mg) | Liquid (µL) | Modifier | DMPT (µL) |
| Control | <u>2.5</u> | <u>60</u> | <u>962</u> | <u>0</u> | <u>0</u> |
| Castor oil/ | 2.5 | 60 | 711 | 0.45 g | 5 |

TABLE 9-continued

Vancomycin containing formulations

| | Formulation | | | | |
|---|---|---|---|---|---|
| | Powder (g) | Vancomycin (mg) | Liquid (µL) | Modifier | DMPT (µL) |
| medium porosity Oleic acid/ high porosity | 2.5 | 60 | 698 | castor oil 0.44 g oleic acid | 6 |
| Linoleic acid/ low porosity | 2.5 | 60 | 934 | 28 µL linoleic acid | 0 |

Figure 10:
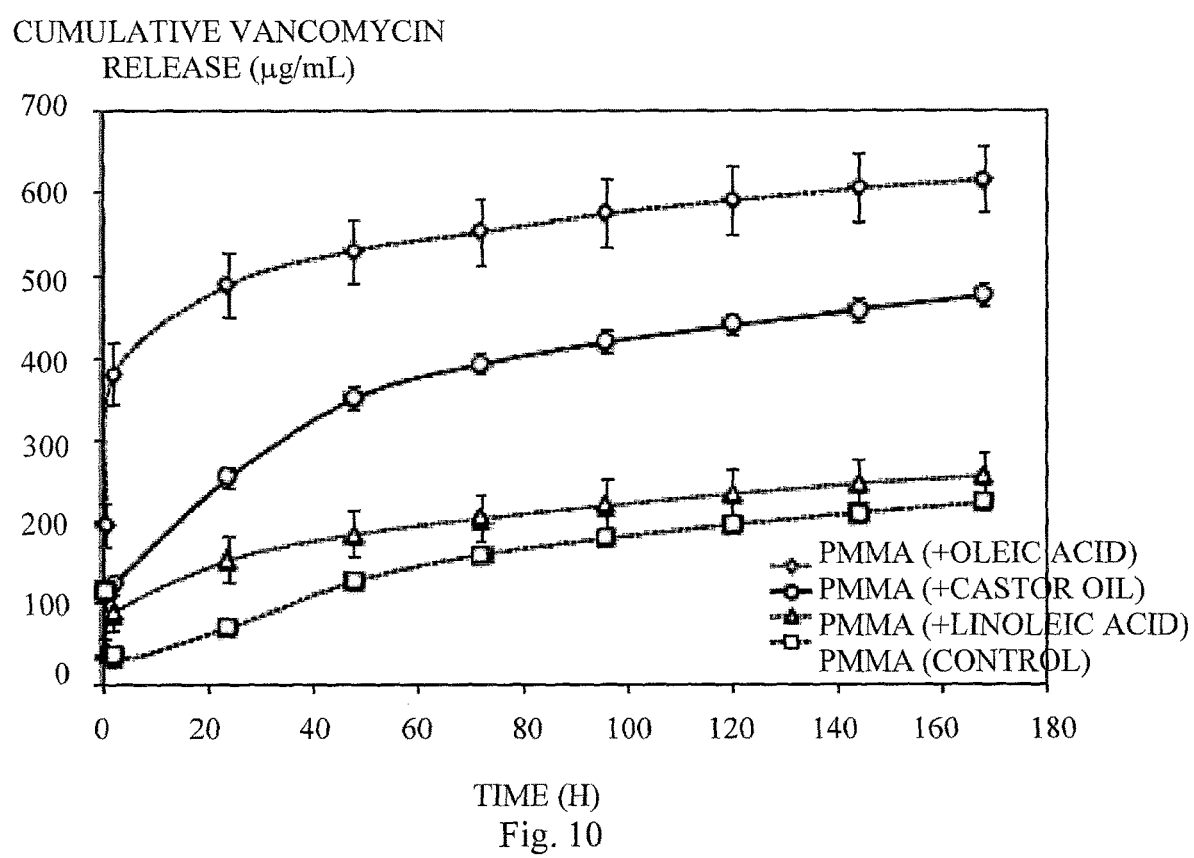
FIG. 10 is a diagram illustrating cumulative Vancomycin release curves from modified bone cements according to the present embodiments compared to standard bone cement.

FIG. 10 shows the cumulative Vancomycin release curves up to 1 week. The release shows a similar trend for all groups, starting with a burst release during the first two hours followed by a slower release. The burst release is more pronounced in formulations with a higher porosity, namely, castor oil and oleic acid. The oleic acid containing specimens exhibited the highest release of Vancomycin due to its relatively high pore content. On the other hand, the linoleic acid containing specimens exhibited the second lowest release of Vancomycin due to their lower pore content. These results indicate that according to the present embodiments, it is possible to control the drug release by changing the nature and/or the concentration of the fatty acid or the triglyceride oil used to prepare the bone cements. The linoleic acid concentration in the bone cement in FIG. 10 was 0.74 w/w of the total cement, or 2.9 v/v of the liquid component.

Example 5. Radiopacity of Cements Containing Castor Oil, Linoleic Acid and Oleic Acid Commercial cements were modified according to examples 1-3 and the radiopacity was investigated in comparison with other commercial formulations. Standard specimens of 1 mm thickness were irradiated with 72 $kV_p$ and the radiopacity was calculated relative to a standard aluminium scale (1 to 5 mm Al). The results shown in FIG. 11 indicate that there is no loss of radiopacity product of modifying the cements, which is because the radiopacity is linked to the radiopaque agent in the powder component, which remains unmodified. The linoleic acid concentration in the bone cement in FIG. 11 was 0.75 w/w of the total cement, or 3 v/v of the liquid component.

Example 6. In Vitro Cell Study of Bone Cements Modified with Linoleic Acid

The cytotoxicity of extracts from bone cements containing linoleic acid was investigated on cells of the osteoblast-like cell line Saos-2 according to ISO 10993-5. The cement preparation was done under sterile conditions. A commercial bone cement formulation (Table 3) was used to which different amounts of linoleic acid were added to the liquid component until a homogeneous solution was achieved. The linoleic acid was filtered using a 0.2 µm syringe-filter prior to use and the cements were prepared according to the embodiments. A first set of experiments was performed using the compositions in Table 10. The concentrations of linoleic acid in the bone cements of Table 10 correspond to 0, 0.5, 0.75 and 1 w/w of the total bone cement, respectively, or 0, 2, 3 and 4 v/v of the liquid component, respectively.

TABLE 10

Formulations containing linoleic acid tested in vitro, % linoleic acid is wt % of powder.

| | Formulation | | |
|---|---|---|---|
| | Powder (g) | Liquid (µL) | Linoleic acid (µL) |
| Control | 10 | 3846 | 0 |
| 0.68% linoleic acid | 10 | 3771 | 75 |
| 1.02% linoleic acid | 10 | 3732 | 113 |
| 1.36% linoleic acid | 10 | 3695 | 151 |

FIG. 12 indicates that the viability of Saos-2 cells at different time points, cultivated in extraction media containing extracts from different cements containing different amounts of linoleic acid according to the present embodiments, are comparable to both the control cement and the control specimens cultivated in normal media.

Figure 13:
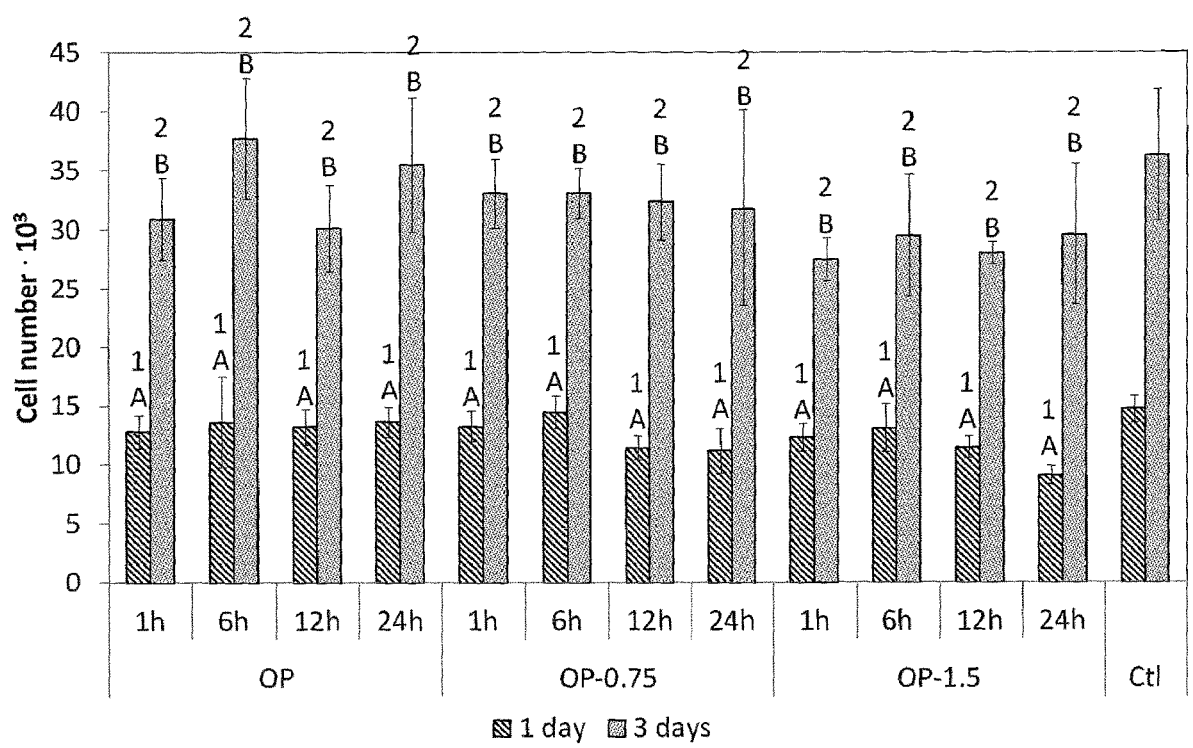
FIG. 13 is a diagram illustrating cell count at 1 and 3 days for Saos-2 cells in contact with extracts from cements in cell media.
Figure 14A:
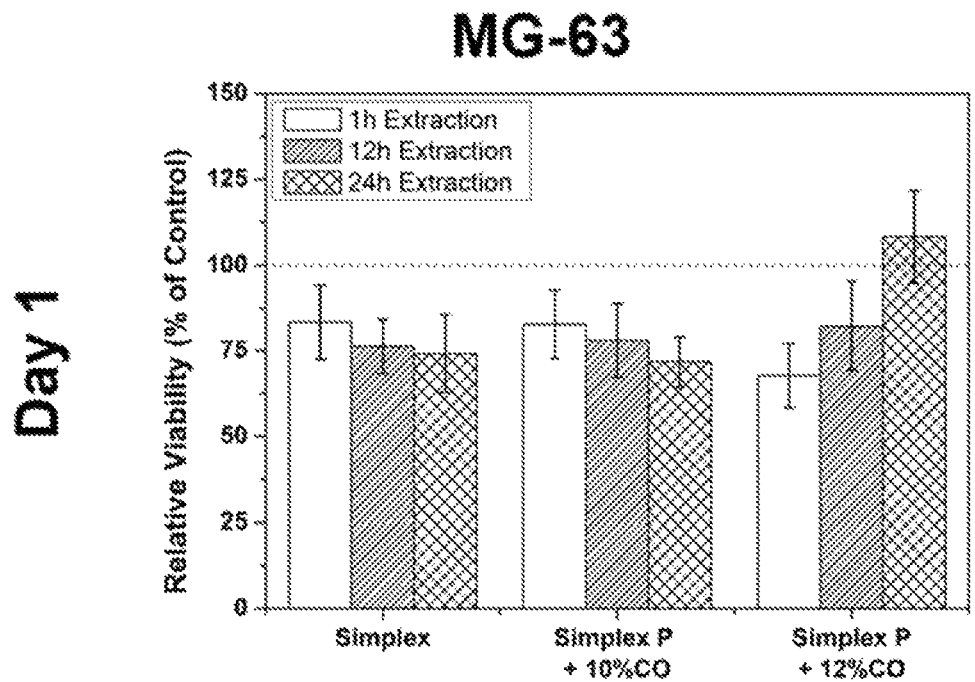
FIGS. 14A-14D illustrate relative cell viability (compared to a control culture in normal medium) of MG-63 (FIGS. 14A and 14B) and Saos-2 cells (FIGS. 14C and 14D), at 1 and 3 days, for extractions taken at 1 h, 12 h, and 24 h from different castor oil containing bone cements. The higher the RFU value, the higher is the cell viability.
Figure 14B:
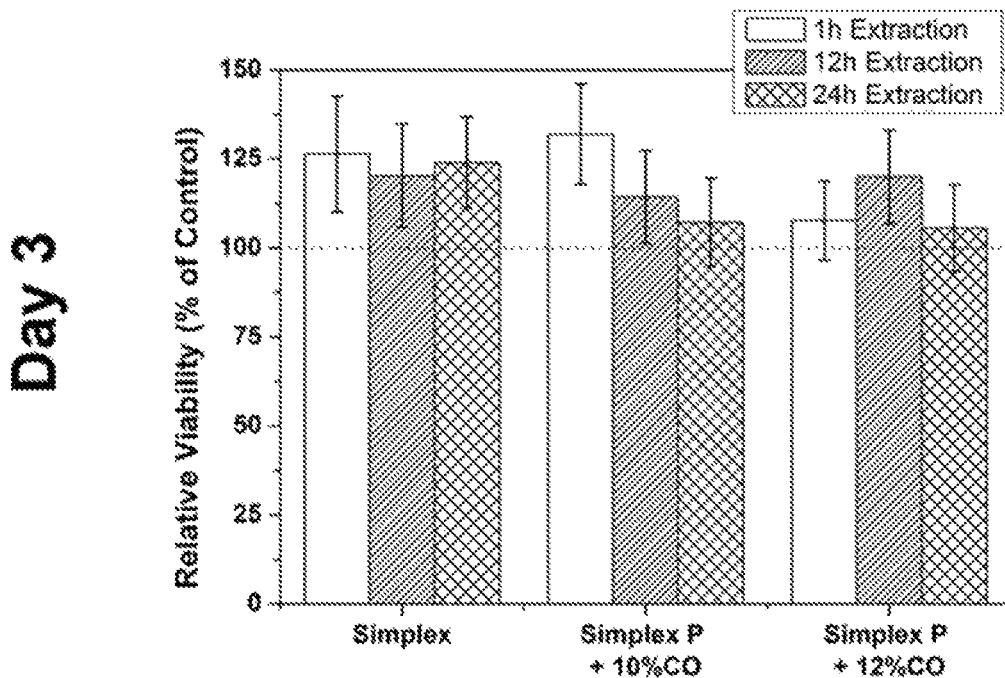
Figure 14C:
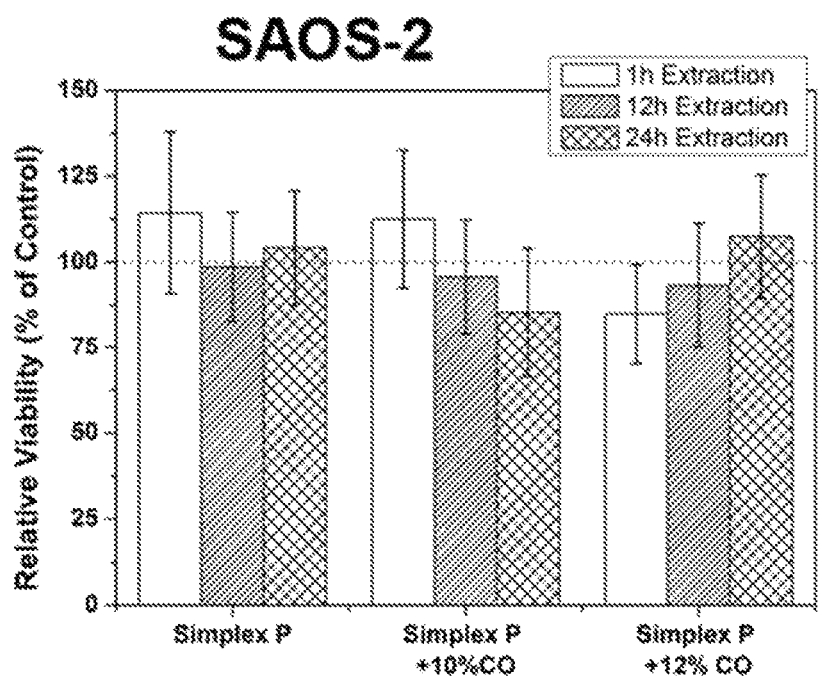
Figure 14D:
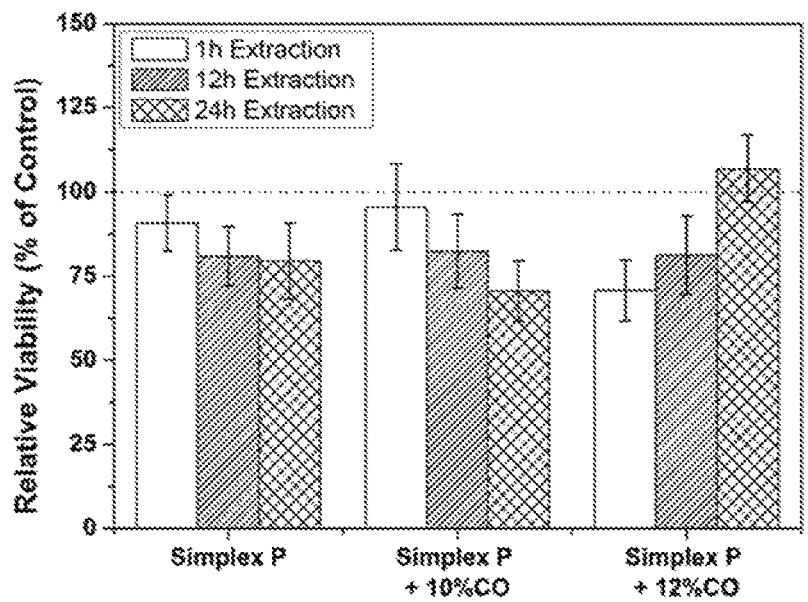

A second set of experiments was performed using linoleic acid concentrations of 0.75 and 1.5% of total bone cement, corresponding to 3 and 6 v/v of the liquid component, respectively. The modified cements showed no difference in cell viability in comparison with the control, as shown in FIG. 13.

Example 7. In Vitro Cell Study of Bone Cements Modified with Castor Oil

The cytotoxicity of extracts from bone cements containing castor oil was investigated on cell lines MG-63 and Saos-2 according to ISO 10993-5. The cement preparation was done under sterile conditions. A commercial bone cement formulation (Table 3) was used to which different amounts of castor oil were added to the liquid component according to Table 11 until a homogeneous solution was achieved. The castor oil was filtered using a 0.2 µm syringe-filter prior to use and the cements were prepared according to the present embodiments.

TABLE 11

Formulations containing castor oil tested in vitro

| | Formulation | | | |
|---|---|---|---|---|
| | Powder (g) | $BaSO_4$ (g) | Liquid (µL) | DMPT (µL) |
| Control | 9 | 1 | 5000 | 0 |
| 10% castor oil | 9 | 1 | 3771 | 20 |
| 12% castor oil | 9 | 1 | 3695 | 25 |

| | Formulation | | | |
|---|---|---|---|---|
| | Castor oil (g) | Young's modulus (MPa) | Strength (MPa) | # of specimens |
| Control | 0 | 1628±44 | 86 | 10 |
| 10% castor oil | 75 | 1121 ± 59 | 40 | 8 |
| 12% castor oil | 151 | 481 ± 70 | 25 | 5 |

FIG. 14 indicates that the viability of MG-63 and Saos-2 cells at different time points, cultivated in extraction media containing extracts from different cements containing different amounts of castor oil according to the present embodiments, are comparable to both the control cement and the control specimens cultivated in normal media.

Example 8. Comparison of Mechanical Properties of Bone Cements Modified with Castor Oil when First Dissolved in the Liquid or when Added after 30 Seconds of Polymerization Example 8 was done in regard of Example 1 in order to solve the issue on whether the castor oil is better dissolved in the liquid component or mixed with the cement during the setting reaction, 30 seconds after mixing the powder and the liquid components. Two formulations (Table 12) were tested. Both formulations were prepared twice, one in which the castor oil was dissolved in the liquid component previous to mixing the powder and another one in which the castor oil was added to the cement 30 seconds after mixing the liquid and the powder components and mixed again for extra 30 seconds.

TABLE 12

Formulations containing castor oil tested.

| | Formulation | | | |
|---|---|---|---|---|
| | Powder (g) | Liquid (μL) | DMPT (μL) | Castor oil (g) |
| 11.5% castor oil; E = 1000 MPa | 10 | 3199 | 14 | 1.15 |
| 17.8% castor oil; E = 500 MPa | 10 | 2845 | 21 | 1.78 |

Figure 15:
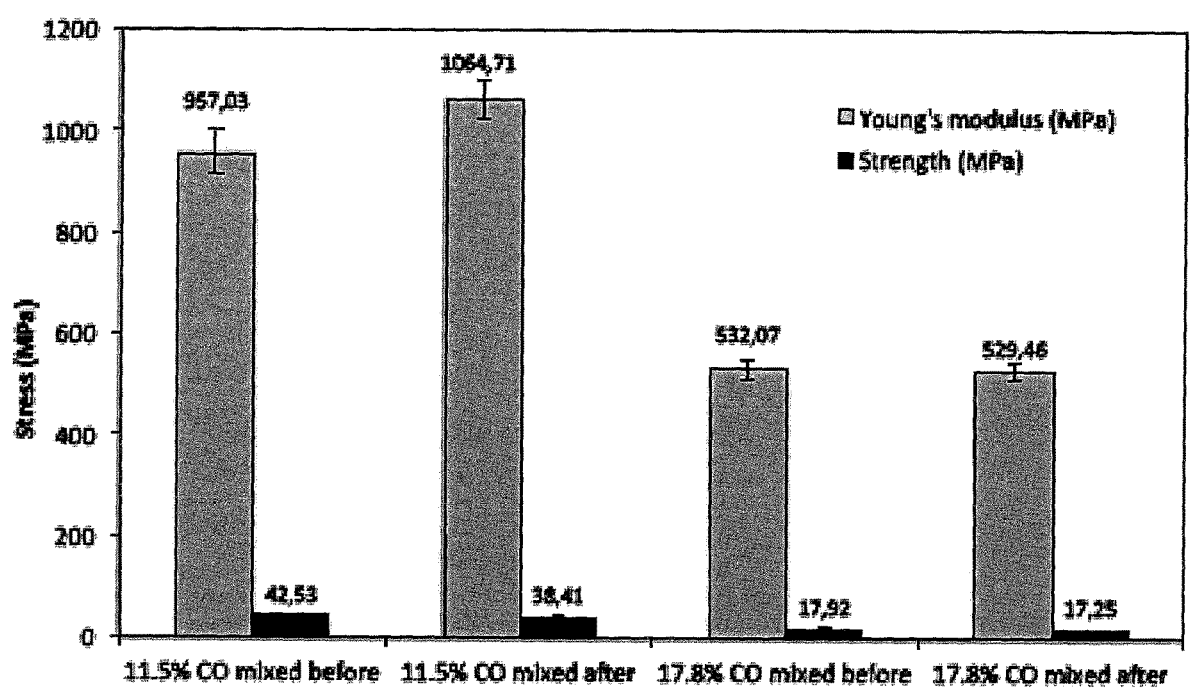
FIG. 15 illustrates a comparison of the Young's modulus and strength of bone cements modified with castor oil when the castor oil is first dissolved in the liquid or added to the setting cement after 30 seconds of mixing.

The results are shown in FIG. 15, which suggests that there is no difference in the mechanical properties whether the castor oil is premixed with the liquid or added after 30 seconds. However, handling is easier when the modifier is premixed in the liquid phase rather than having a third component (an additional mixing component is introduced for the user and a homogeneous mixture is much more difficult to achieve due to the higher viscosity), which would also increase the costs of the product.

Figure 16:
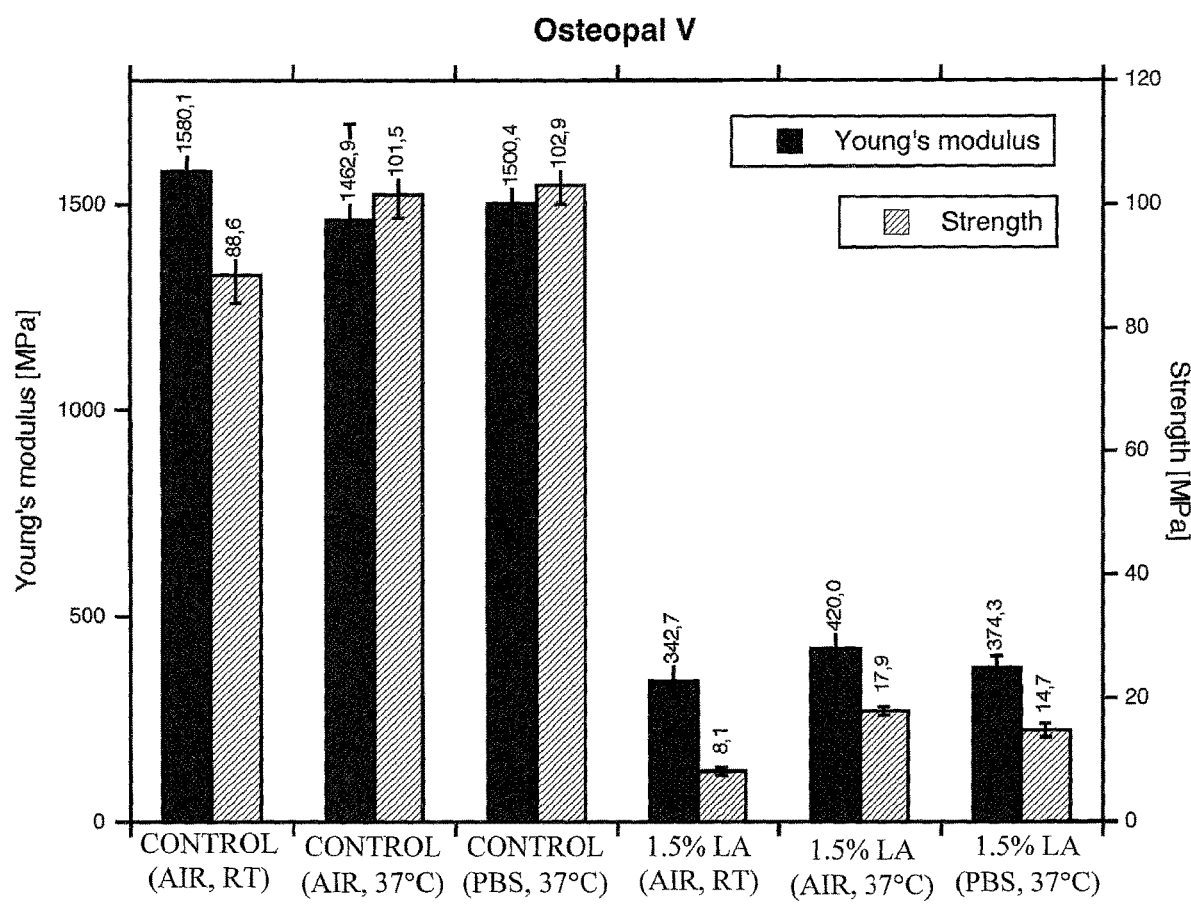
FIG. 16 illustrates a comparison of the Young's modulus and strength of bone cements modified with linoleic acid for different storage conditions prior to testing.

Example 9. The Effect of Storage on the Mechanical Properties of Unmodified and Modified Cements A commercial bone cement formulation (Table 3) was used to which 1.5 wt % (of total weight) linoleic acid were added to the liquid component until a homogeneous solution was achieved, corresponding to 6 v/v of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature or at 37° C., in air or in PBS, and tested after 24 hours using an AGS-H universal materials testing machine (Shimadzu, Kyoto, Japan) at a crosshead displacement rate of 20 mm/min. The Young's modulus and the strength were obtained from the load-versus-displacement curves. The results are shown in FIG. 16, indicating that storage at 37° C. gives a similar elastic modulus but a higher strength of both unmodified and modified cements. This is one example of the variability in mechanical properties due to testing conditions.

Example 10. Mechanical Properties of Linoleic Acid Modified Cements Using Larger Specimens and Pre-Conditioning, on their Own and in Bovine Bone Four groups of cements including one unmodified with composition according to Table 3 (OP) and three modified with 0.5 (OP-0.50), 0.75 (OP-0.75), and 1.50 (OP-1.50) wt % linoleic acid (with respect to the total weight) were prepared. This corresponded to 2, 3 and 6 v/v of the liquid component, respectively. Specimen of 10 mm in diameter and 20 mm high were prepared. Bovine tibiae were used to prepare bone cores of the same size, which were later injected with the cements after removal of the bone marrow, resulting in composite specimens. Specimens were stored in PBS at 37° C. for 24 h before testing. Uniaxial compression testing was performed under displacement control at 6 mm/min in a materials testing machine. Five preconditioning cycles (0.1-0.5% strain) were applied before loading the specimens to failure. Testing was carried out at room temperature. The elastic modulus (E) was defined as the slope of the stress-strain curve between 0.2 and 0.4% strain. The yield stress ($\sigma_y$) and the yield strain ($\varepsilon_y$) were defined by the 0.2% offset method. The ultimate stress ($\sigma_u$) was defined as the stress at maximum load. The results are shown in Table 13, indicating that a higher elastic modulus can be obtained due to testing conditions, in this case larger specimens and preconditioning are likely to have an effect.

TABLE 13

Summary of experimental compressive properties. Results are given as mean ± standard deviation, with the range given in the parentheses.

| | Cement-only group | | | |
|---|---|---|---|---|
| | OP (n = 10) | OP-0.50 (n = 10) | OP-0.75 (n = 10) | OP-1.50 (n = 10) |
| E [MPa] | 3571 ± 176 (3355-3833) | 2703 ± 230() (2341-3165) | 1878 ± 290() (1232-2150) | 872 ± 92(**) (689-981) |
| $\varepsilon_y$ [%] | 2.03 ± 0.10 (1.86-2.20) | 1.95 ± 0.13 (1.75-2.13) | 1.82 ± 0.15() (1.59-2.09) | 1.73 ± 0.16() (1.50-2.12) |
| $\sigma_y$ [MPa] | 65.2 ± 3.3 (58.6-69.2) | 47.3 ± 3.4() (41.8-51.8) | 30.4 ± 4.9() (21.3-38.7) | 13.2 ± 0.8(**) (11.7-14.6) |
| $\varepsilon_u$ [%] | 5.40 ± 0.31 (4.88-5.86) | 4.71 ± 0.47() (3.99-5.24) | 3.57 ± 0.35() (3.23-4.37) | 3.10 ± 0.09(**) (2.93-3.18) |
| $\sigma_u$ [MPa] | 99.3 ± 6.4 (87.0-107.6) | 70.3 ± 8.2() (56.5-82.5) | 40.4 ± 7.1() (26.8-52.7) | 17.1 ± 1.1(**) (15.5-18.7) |

TABLE 13-continued

Summary of experimental compressive properties. Results are given as mean ± standard deviation, with the range given in the parentheses.

| | Composite group | | | |
|---|---|---|---|---|
| | OP (n = 11) | OP-0.50 (n = 11) | OP-0.75 (n = 10) | OP-1.50 (n = 13) |
| E [MPa] | 3246 ± 729 (2422-4942) | 2834 ± 518 (1799-3622) | 2597 ± 491[*, §] (1969-3346) | 2274 ± 455[*, §] (1401-2869) |
| $\varepsilon_y$ [%] | 1.43 ± 0.15 (1.31-1.80) | 1.49 ± 0.20 (1.25-1.85) | 1.45 ± 0.22 (1.13-1.77) | 1.34 ± 0.07 (1.23-1.52) |
| $\sigma_y$ [MPa] | 39.6 ± 8.6 (29.7-55.0) | 35.8 ± 4.7 (27.2-41.6) | 31.8 ± 3.7[*] (25.0-37.3) | 25.7 ± 4.7[*, §] (17.7-32.0) |
| $\varepsilon_u$ [%] | 4.65 ± 0.60 (3.82-5.59) | 4.60 ± 0.48 (3.88-5.25) | 4.02 ± 0.73[*] (2.88-5.05) | 3.24 ± 0.17[*] (3.01-3.70) |
| $\sigma_u$ [MPa] | 63.4 ± 12.2 (46.4-81.4) | 56.8 ± 8.8 (37.2-66.6) | 47.5 ± 5.2[*] (38.2-58.0) | 35.1 ± 5.4[*, §] (25.9-42.8) |

[*]significantly different from OP (composite group).
[**]significantly different from OP (cement-only group).

Example 12. Bone Cement Modified Using Methyl Linoleate

A commercial bone cement formulation (Table 3) was used to which different amounts of methyl linoleate were added to the liquid component until a homogeneous solution was achieved. Extra DMPT was also added to compensate upon removing part of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves. The results are shown in Table 14, indicating that the mechanical properties can be tailored also using methyl linoleate.

TABLE 14

Osteopal V modified with methyl linoleate (wt % of total cement).

| | Methyl linoleate [wt %] | | | |
|---|---|---|---|---|
| | 0.18 (n = 5) | 0.37 (n = 6) | 0.55 (n = 5) | 0.91 (n = 5) |
| E [MPa] | 1585 ± 82 | 1563 ± 127 | 1143 ± 66 | 456 ± 16 |
| $\sigma_{2\%}$ [MPa] | 66.2 ± 1.8 | 53.3 ± 1.3 | 32.6 ± 1.4 | 9.8 ± 0.3 |
| $\sigma_u$ [MPa] | 66.4 ± 1.9 | 54.1 ± 1.3 | 33.8 ± 1.6 | 10.1 ± 0.3 |

Commercial formulation Simplex P was also modified with methyl linoleate, showing the potential for tailoring the mechanical properties of also this cement, see Table 15.

TABLE 15

Simplex P modified with methyl linoleate (wt % of total cement).

| | Methyl linoleate [wt %] | | | | | |
|---|---|---|---|---|---|---|
| | 0.68 (n = 6) | 1.02 (n = 6) | 1.35 (n = 6) | 1.69 (n = 6) | 2.02 (n = 6) | 2.69 (n = 6) |
| E [MPa] | 1477 ± 209 | 1367 ± 68 | 1131 ± 27 | 947 ± 41 | 502 ± 27 | 307 ± 7 |
| $\sigma_{2\%}$ [MPa] | 63.4 ± 1.5 | 48.5 ± 1.9 | 30.7 ± 0.4 | 22.5 ± 0.3 | 12.6 ± 0.3 | 6.6 ± 0.1 |
| $\sigma_u$ [MPa] | 63.6 ± 1.5 | 49.2 ± 2.0 | 31.7 ± 0.5 | 23.1 ± 0.3 | 12.6 ± 0.2 | 6.7 ± 5.7 |

Example 12. Bone Cement Modified Using Linseed Oil

A commercial bone cement formulation (Table 3) was used to which different amounts of linseed oil were added to the liquid component until a homogeneous solution was achieved. Extra DMPT was also added to compensate upon removing part of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves. The results are shown in FIG. 19, indicating that the mechanical properties can be tailored also using linseed oil.

Commercial formulation Simplex P was also modified with linseed oil, showing the potential for tailoring the mechanical properties of also this cement, see FIG. 20.

Example 13. Bone Cement Modified Using Tung Oil

A commercial bone cement formulation (Table 3) was used to which different amounts of tung oil were added to the liquid component until a homogeneous solution was achieved. Extra DMPT was also added to compensate upon removing part of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves. The results are shown in FIG. 21, indicating that the mechanical properties can be tailored also using tung oil.

Commercial formulation Simplex P was also modified with tung oil, showing the potential for tailoring the mechanical properties of also this cement, see FIG. 22.

Example 14. Bone Cement Modified Using Ricinoleic Acid

A commercial bone cement formulation (Table 3) was used to which different amounts of ricinoleic acid were added to the liquid component until a homogeneous solution was achieved. Extra DMPT was also added to compensate upon removing part of the liquid component. The powder and liquid components were combined at room temperature in a 50 mL centrifuge tube and mixed for 30 seconds with a cap mixer. The specimens were molded in Teflon® molds with a size of 6 mm diameter and 12 mm height according to ASTM F451-08 standard. The specimens were stored at room temperature and tested after 24 hours using an AGS-H universal materials testing machine (Shimadzu, Kyoto, Japan) at a crosshead displacement rate of 20 mm/min. The Young's modulus and the strength were obtained from the load-versus-displacement curves. The results are shown in FIG. 23, indicating that the mechanical properties can be tailored also using ricinoleic acid.

Commercial formulation Simplex P was also modified with ricinoleic acid, showing the potential for tailoring the mechanical properties of also this cement, see FIG. 24.

Example 15. Maximum Polymerization Temperature of Modified Cements

The maximum temperature during setting was measured according to ASTM F451, using a thermocouple. The modified cements always showed lower maximum temperature than the control. The concentrations of oils in Table 16 are in % of powder, which for linoleic acid (LA) correspond to 0.73 w/w of total bone cement and 3 v/v of the liquid component for Osteopal and 1.77 w/w of total bone cement and 5.7 v/v of the liquid component for Simplex.

TABLE 16

Maximum temperature of different Osteopal cements and Simplex cements

| Osteopal | | | | |
|---|---|---|---|---|
| | Control | 17.8% CO | 1% LA | 18.3% RA |
| Maximum temperature | 42° C. | 30° C. | 30° C. | 29° C. |

| Simplex | | | | |
|---|---|---|---|---|
| | Control | 23.4% CO | 2.6% LA | 24.4% RA |
| Maximum temperature | 44° C. | 30° C. | 30° C. | 27° C. |

Example 16. In Vivo Biocompatibility

The biocompatibility was assessed in Sprague Dawley rats, using a subcutaneous model. Cements (Osteopal V) modified with castor oil (18%) and linoleic acid (1.5% w/w of total bone cement or 6 v/v of the liquid component) were used and the inflammatory response was compared to control cement (unmodified cement). 6-8 specimens were used per group and time point. No differences in biocompatibility were found between control and test specimen at 1 and 4 weeks of implantation.

Example 17. Mechanical Properties of Modified Cements Using Higher Amount of Linoleic Acid A commercial bone cement formulation (Table 3) was used to which different amounts of linoleic acid were added to the liquid component until a homogeneous solution was achieved. The power and liquid components were combined at room temperature in a 50 ml centrifuge tube and mixed for 30 s with a cap mixer. The specimens were molded in Teflon® molds with a size of 6 mm diameter and 12 mm height according to ASTM F451-08 standard. The specimens were stored in PBS at 37° C. and tested after 24 hours using an AGS-H universal materials testing machine (Shimadzu, Kyoto, Japan) at a crosshead displacement rate of 20 mm/min. The Young's modulus was obtained from the load-versus-displacement curves. 6 vol % of linoleic acid (1.5 w/w of total bone cement) gave a Young's modulus of 400±57 MPa, 10 vol % of linoleic acid (2.5 w/w of total bone cement) gave a Young's modulus of 201±75 MPa, and 15 vol % of linoleic acid (3.8 w/w of total bone cement) gave a Young's modulus of 185±22 MPa.

Example 18. Injection Test: Continuous Injection without Resistance

This test was firstly done with a speed of 3 mm/min but for the sample with linoleic acid (LA) the syringe was empty before reaching force limit. It was therefore necessary to determine the optimal speed.

Three rates were tested: 2, 1 and 1.5 mm/min. With 2 mm/min the syringe was also empty. With 1 and 1.5 mm/min the force limit reached before it was empty but with 1 mm/min a huge part of the cement stayed into the syringe. The speed of 1.5 mm/min was chosen to do this test.

Figure 25:
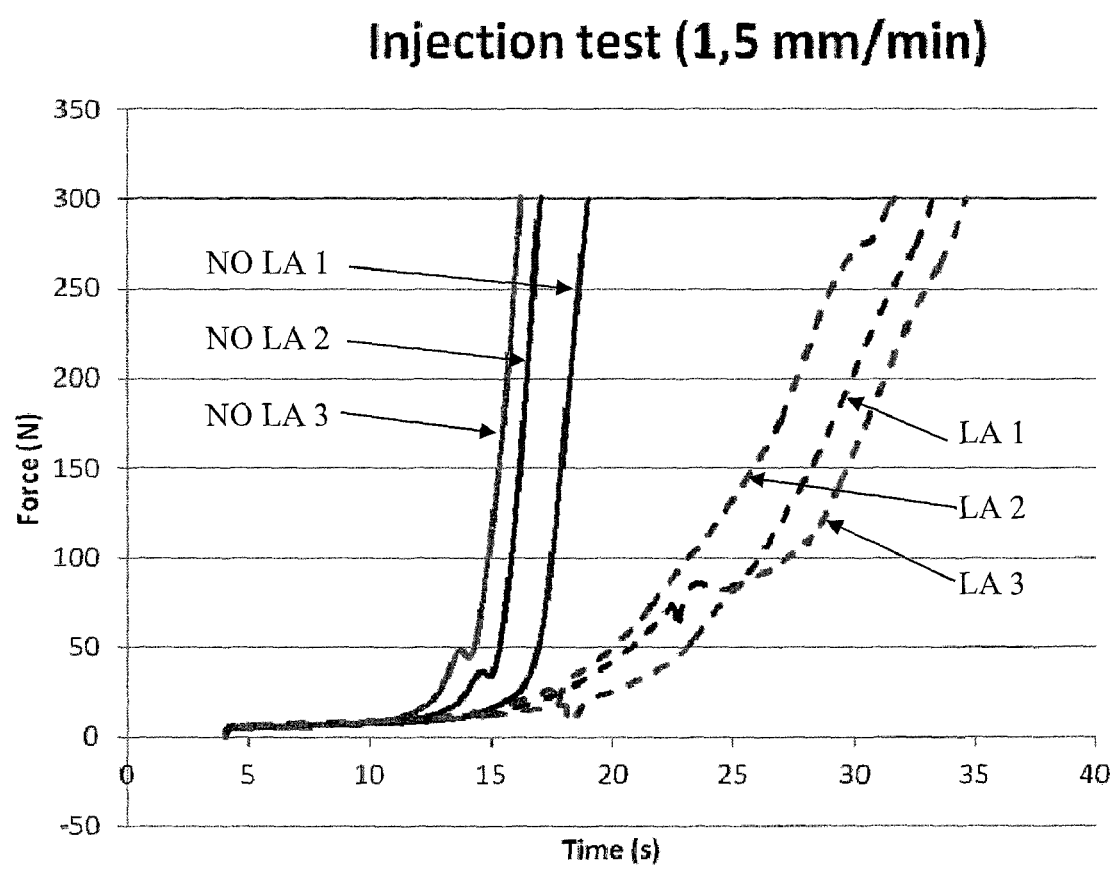
FIG. 25 illustrates injection forces of PMMA bone cement with and without linoleic acid.

The results of an injection test without resistance at a speed of 1.5 mm/min are shown in FIG. 25 (solid line: without LA, dotted line: with 1.5 wt % LA, 6 v/v of the liquid component). The downward peaks observed in the curves were due to air bubbles caught into the cement. For all the cements, with and without additive, the force was stable around 5-7 N before increasing. The increase was sudden for the samples without LA around 15 min after mixing. For the samples with LA the curve increased slowly after 15-20 min.

Figure 26:
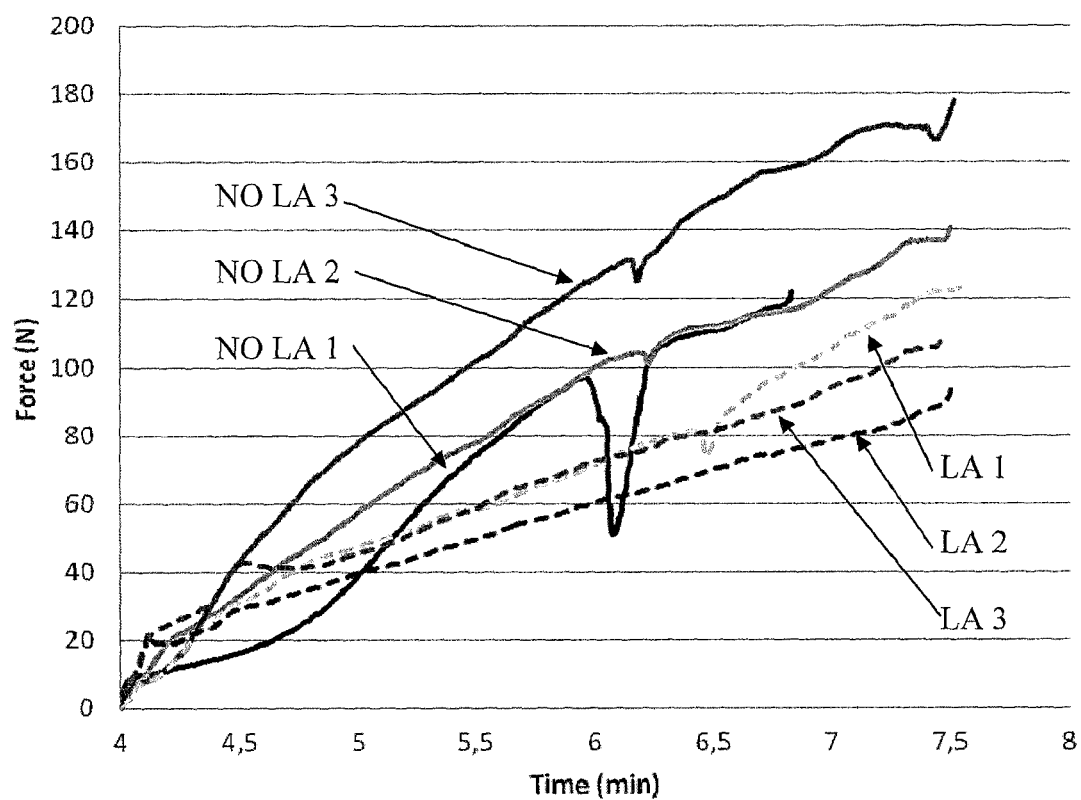
FIG. 26 illustrates injection forces of injection of PMMA bone cement with and without linoleic acid into sawbone in a set-up simulating physiological conditions.

Example 19. Injection Test: Injection into Sawbone in a Set-Up Simulating Physiological Conditions Injection tests were performed in sawbones and under physiological conditions (in PBS at 37° C.). The injection was done through a 13G cannula (100 mm in length) directly into the sawbone where a 2.5 mm canal had been created to simulate a blood vessel. The test started at 4 min after cement mixing and was stopped when the forced reached above 150 N, which is assumed to be the maximum force possible by hand. Evaluation of the cement spread in the sawbone block was done using microCT By adding small amounts of linoleic acid (1.5 wt %, 6 v/v of the liquid component) the injection force decreased by approximately 40% (FIG. 26, Solid lines: unmodified cement. Dotted lines: modified cement.). Since the force decreased with the modified cement, the injection time also increased by approximately 50% which corresponded to 1.5 min. The microCT images showed no significant differences in cement spread between the cements. The sphericity factor was 0.653 for the unmodified vs 0.700 for the modified cement.

It is important that injection of cement during vertebroplasty is done in a safe and controlled way. By modifying commercially available PMMA cement with a small amount of linoleic acid, the injection force decreased and the injection time increased, without changing the spread pattern of the cement during injection. The results obtained with the modified cement shows that it is easy to inject and cohesive enough to avoid uncontrolled leakage during injection.

Example 20. Mechanical Properties of Modified Cements in a Human Ex Vivo Model

Compression tests were performed on the modified (low-modulus) cement vs commercially available cement in a human ex vivo model in order to evaluate whether augmentation with low-modulus cement adequately restores stiffness and strength of osteoporotic vertebrae.

Low-modulus cement (elastic modulus 872±92 MPa) was produced by the addition of small amounts of linoleic acid (6 v/v of the liquid component) to commercially available acrylic bone cement for vertebroplasty. The same commercially available cement was used as control (standard) cement (elastic modulus 3571±176 MPa). Wedge fractures were induced in 24 osteoporotic cadaveric vertebrae, which were then augmented with either standard or low-modulus acrylic cement, and finally fractured again. Strength and stiffness were calculated from the load-displacement data and microCT was used for monitoring purposes as well as to determine bone morphological parameters.

The vertebral bodies had an average BMD of 134±40 mg HA/cm$^3$ and a BV/TV of 0.18±0.04. Both standard and low-modulus cement were found to increase the strength of the vertebrae after fracture and augmentation (FIG. 27 left, presents the percentage change in strength of osteoporotic vertebral bodies after fracture and augmentation with standard and low-modulus cement.). Low-modulus cement was found to restore the stiffness, while standard cement was found to give an increase in stiffness, and osteoporotic vertebrae augmented with standard cement were on average 55% stiffer than those augmented with low-modulus cement (FIG. 27 right, presents the percentage change in stiffness of osteoporotic vertebral bodies after fracture and augmentation with standard and low-modulus cement.).

Vertebroplasty with low-modulus cement was found to be biomechanically satisfactory in terms of restoring the stiffness and increasing the strength of osteoporotic single vertebrae. Future use of this type of cement in the clinical setting could potentially reduce the risk of adjacent level fracture and its associated morbidity.

While the invention has been described in connection with what is presently considered to be the most practical and preferred embodiments, it is to be understood that the invention is not to be limited to the disclosed embodiments On the contrary, it is intended to cover various modifications and equivalent arrangements. Note that the properties of the cements may be affected by e.g. the quality of the modifier and testing conditions.

REFERENCES

Beck, S. and A. Boger (2009). "Evaluation of the particle release of porous PMMA cements during curing". *Acta Biomater* 5(7): 2503-2507.
Boger, A., A. Bisig, et al. (2008). "Variation of the mechanical properties of PMMA to suit osteoporotic cancellous bone". *J Biomater Sci Polym Ed* 19(9): 1125-1142.
Boger, A., M. Bohner, et al. (2008). "Properties of an injectable low modulus PMMA bone cement for osteoporotic bone". *J Biomed Mater Res B Appl Biomater* 86B(2): 474-482.
Bruens, M. L., H. Pieterman, et al. (2003). "Porous polymethylmethacrylate as bone substitute in the craniofacial area". *J Craniofac Surg* 14(1): 63-68.
Kong X., Narine S. S. (2008) "Sequential interpenetrating polymer networks produced from vegetable oil based polyurethane and poly(methyl methacrylate)". *Biomacromolecules* 9:2221-2229.
Lam W. M., Pan H. B., et al. (2010) "In vitro characterization of low modulus linoleic acid coated strontium substituted hydroxyapatite containing PMMA bone cement". *J Biomed Mater Res B Appl Biomater* 96(1): 76-83.
Oliveira Vierira da Cunha F., Roesler Melo D. H. (2004) "Study of castor oil polyurethane-poly(methyl methacrylate) semi-interpenetrating polymer networks (SIPN) reaction parameters using a $2^3$ factorial experimental design". *Materials Research* 7(4):539-543.
Seniha Güner F., Yağci Y., et al. (2006). "Polymers from triglyceride oils". *Prog Polym Sci* 31:633-670.
Shimko, D. A. and E. A. Nauman (2007). "Development and characterization of a porous poly(methyl methacrylate) scaffold with controllable modulus and permeability". *J Biomed Mater Res B Appl Biomater* 80(2): 360-369.
Shimko, D. A., K. K. White, et al. (2003). "A device for long term, in vitro loading of three-dimensional natural and engineered tissues". *Ann Biomed Eng* 31(11): 1347-1356.
van Mullem, P. J., de Wijn J. R., et al. (1988). "Porous acrylic cement: evaluation of a novel implant material". *Ann Plast Surg* 21(6): 576-582.
Vázquez B., Deb S., et al. (2001) "Characterization of new acrylic bone cements prepared with oleic acid derivatives". *J Biomed Mater Res* 63(2):88-97.

The invention claimed is:

1. An injectable composition for a bone cement material comprising a dry powder component comprising prepolymerized poly(methyl methacrylate) (PMMA) or a copolymer of PMMA and a pharmaceutically acceptable polymer, a liquid component comprising methyl methacrylate (MMA) monomer, and a modifier, wherein said modifier is linoleic acid or a salt thereof and is present in a concentration of 0.5 to 12 vol % of said liquid component and a concentration of 0.25 to 3 wt % of total bone cement material, and wherein the bone cement material has a Young's modulus of less than 1500 MPa.

2. The injectable composition according to claim 1, wherein said modifier is present in a concentration of 1 to 10 vol % of said liquid component.

3. The injectable composition according to claim 2, wherein said modifier is present in a concentration of 2 to 10 vol % of said liquid component.

4. The injectable composition according to claim 3, wherein said modifier is present in a concentration of 2 to 6 vol % of said liquid component.

5. The injectable composition according to claim 1, wherein said modifier is present in a concentration of 0.25 to 2.5 wt % of said total bone cement material.

6. The injectable composition according to claim 5, wherein said modifier is present in a concentration of 0.5 to 2.5 wt % of said total bone cement material.

7. The injectable composition according to claim 6, wherein said modifier is present in a concentration of 0.5 to 1.5 wt % of said total bone cement material.

8. The injectable composition according to claim 1, wherein said modifier is present in said liquid component.

9. The injectable composition according to claim 1, further comprising a radical initiator, and a chemical activator.

10. The injectable composition according to claim 1, further comprising a pharmaceutically active agent selected from a group consisting of an antibiotic, a growth factor, a bisphosphonate, an anti-inflammatory agent, an analgesic agent and a cytotoxic agent, or a mixture thereof.

11. The injectable composition according to claim 1, wherein said injectable composition has a liquid-to-powder ratio between said liquid component and said dry powder component in a range of 0.1 to 1.5 mL/g.

12. The injectable composition according to claim 1, wherein said dry powder component has a particle size in a range of 10 to 1000 μm.

13. The injectable composition according to claim 1, further comprising a radiocontrast agent at a concentration of 5 to 60 wt % of said dry powder component.

14. A method of producing the injectable composition for a bone cement material according to claim 1, the method comprising mixing the dry powder component, the liquid component and the modifier to form said bone cement material, wherein said modifier is linoleic acid or a salt thereof, and is present in a concentration of 0.5 to 12 vol % of said liquid component and a concentration of 0.25 to 3 wt % of total bone cement material.

15. The method according to claim 14, wherein mixing said dry powder component, said liquid component and said modifier comprises:
mixing said liquid component comprising MMA monomer and a chemical activator with said modifier to form a homogenous solution; and
mixing said homogenous solution with the dry powder component comprising i) PMMA or a copolymer of PMMA and a pharmaceutically acceptable polymer, ii) a radical initiator, and iii) optionally a radiocontrast agent to form said bone cement material.

16. A kit for producing the injectable composition for a bone cement material according to claim 1, said kit comprising:
a container comprising the liquid component;
a container comprising linoleic acid or a salt thereof as a modifier at an amount corresponding to a concentration of 0.5 to 12 vol % of said liquid component when mixing said modifier and said liquid component;
a container comprising the dry powder component;
instructions for mixing said modifier and said liquid component to form a homogenous solution; and
instructions for mixing said dry powder component and said homogenous solution to form said injectable composition for said bone cement material,
wherein the linoleic acid or salt thereof is contained in the container in an amount effective to provide linoleic acid or salt thereof in the bone cement material in an amount of 0.25 to 3 wt % of total bone cement material.

17. A method of producing a subject-specific injectable composition for a bone cement material according to claim 1, said method comprising:
determining a target Young's modulus of said bone cement material of less than 1500 MPa based on a bone mineral density of a subject;
determining a concentration of a modifier within a range of 0.5 to 12 vol % of the liquid component and a concentration of 0.25 to 3 wt % of total bone cement material, both based on said target Young's modulus; and
mixing the dry powder component, said liquid component and said modifier to form said bone cement material, wherein said modifier is linoleic acid or a salt thereof and is present in said determined concentrations.

18. The method according to claim 17, wherein determining said concentrations of said modifier comprises determining said concentration of said modifier within said range of 0.5 to 12 vol % of said liquid component and a concentration of 0.25 to 3 wt % of total bone cement material, both based on said target Young's modulus and a control Young's modulus for said bone cement material.

19. The injectable composition according to claim 1, wherein said dry powder component comprises a copolymer of PMMA and polystyrene.

20. The injectable composition according to claim 9, wherein said radical initiator is benzoyl peroxide (BPO), and said chemical activator is N,N-dimethyl-p-toluidine (DMPT).

21. The injectable composition according to claim 11, wherein said injectable composition has a liquid-to-powder ratio between said liquid component and said dry powder component in a range of 0.3 to 0.9 mL/g.

22. The injectable composition according to claim 12, wherein said dry powder component has a particle size in a range of 50 to 300 μm.

* * * * *

UNITED STATES PATENT AND TRADEMARK OFFICE
CERTIFICATE OF CORRECTION

| | |
|---|---|
| PATENT NO. | : 10,603,403 B2 |
| APPLICATION NO. | : 14/783019 |
| DATED | : March 31, 2020 |
| INVENTOR(S) | : Cecilia Persson et al. |

Page 1 of 1

It is certified that error appears in the above-identified patent and that said Letters Patent is hereby corrected as shown below:

On the Title Page

Item (30), change "1350437" to --1350437-8--.

Signed and Sealed this
Seventh Day of July, 2020

Andrei Iancu
*Director of the United States Patent and Trademark Office*